(12) United States Patent
Celia et al.

(10) Patent No.: US 9,981,982 B2
(45) Date of Patent: May 29, 2018

(54) SUPEROLEOPHOBIC AND/OR SUPERHYDROPHOBIC MATERIAL, PROCESS FOR PREPARING SAME AND APPLICATIONS THEREOF

(71) Applicants: CENTRE NATIONAL DE LA RECHERCHE SCIENTIFIQUE, Paris (FR); UNIVERSITE NICE SOPHIA ANTIPOLIS, Nice (FR)

(72) Inventors: Elena Celia, Cagnes sur Mer (FR); Jeanne Hélène Suzanne Tarrade, Cannes (FR); Thierry Darmanin, Nice (FR); Frédéric Guittard, Nice (FR)

(73) Assignees: CENTRE NATIONAL DE LA RECHERCHE SCIENTIFIQUE, Paris (FR); UNIVERSITE NICE SOPHIA ANTIPOLIS, Nice (FR)

( * ) Notice: Subject to any disclaimer, the term of this patent is extended or adjusted under 35 U.S.C. 154(b) by 0 days. days.

(21) Appl. No.: 14/893,102

(22) PCT Filed: May 21, 2014

(86) PCT No.: PCT/FR2014/000113
§ 371 (c)(1),
(2) Date: Nov. 23, 2015

(87) PCT Pub. No.: WO2014/188089
PCT Pub. Date: Nov. 27, 2014

(65) Prior Publication Data
US 2016/0096845 A1 Apr. 7, 2016

(30) Foreign Application Priority Data
May 23, 2013 (FR) ..................... 13 01175

(51) Int. Cl.
| | | |
|---|---|---|
| C07D 495/04 | (2006.01) | |
| C07D 491/056 | (2006.01) | |
| C07D 497/04 | (2006.01) | |
| B32B 5/14 | (2006.01) | |
| B32B 15/08 | (2006.01) | |
| B32B 15/18 | (2006.01) | |
| B32B 15/20 | (2006.01) | |
| C09D 165/00 | (2006.01) | |
| C09D 5/08 | (2006.01) | |
| C08J 5/18 | (2006.01) | |
| C25D 13/20 | (2006.01) | |
| C25D 13/22 | (2006.01) | |
| C09D 5/44 | (2006.01) | |
| C10M 107/46 | (2006.01) | |
| C09D 5/16 | (2006.01) | |

(52) U.S. Cl.
CPC .............. *C07D 495/04* (2013.01); *B32B 5/14* (2013.01); *B32B 15/08* (2013.01); *B32B 15/18* (2013.01); *B32B 15/20* (2013.01); *C07D 491/056* (2013.01); *C07D 497/04* (2013.01); *C08J 5/18* (2013.01); *C09D 5/08* (2013.01); *C09D 5/1662* (2013.01); *C09D 5/1693* (2013.01); *C09D 5/4476* (2013.01); *C09D 165/00* (2013.01); *C10M 107/46* (2013.01); *C25D 13/20* (2013.01); *C25D 13/22* (2013.01); *B32B 2307/714* (2013.01); *B32B 2307/73* (2013.01)

(58) Field of Classification Search
None
See application file for complete search history.

(56) References Cited

U.S. PATENT DOCUMENTS

| | | | |
|---|---|---|---|
| 2008/0015298 A1 | 1/2008 | Xiong et al. | |
| 2008/0248263 A1* | 10/2008 | Kobrin | C08J 7/16 428/195.1 |
| 2008/0268233 A1 | 10/2008 | Lawin et al. | |

(Continued)

FOREIGN PATENT DOCUMENTS

| | | |
|---|---|---|
| EP | 2 092 026 | 8/2009 |
| EP | 2 118 189 | 11/2009 |

(Continued)

OTHER PUBLICATIONS

Darmanin et al. JACS 2011, 133, 15627-15634.*
Morgenthaler et al. Langmuir—The ACS Journal of Surfaces and Colloids, vol. 19 (25):10459-10462 (2003).*
McHale Contact Angle, Wettability and Adhesion, Chapter: Superhydrophobicity, Localized Parameters and Gradient Surfaces vol. 6:219-233 (2009).*
Darmanin et al. Langmuir 26(22): 17596-17602 (2010).*
Darmanin et al., "Hydrocarbon versus Fluorocarbon in the Electrodeposition of Superhydrophobic Polymer Films", Langmuir, vol. 26, No. 22, Nov. 16, 2010, pp. 17596-17602.
Tarrade et al., "Super liquid-repellent properties of electrodeposited hydrocarbon and fluorocarbon copolymers", RSC Advances, vol. 3, No. 27, May 8, 2013, pp. 10848-10853.

(Continued)

*Primary Examiner* — Samantha L Shterengarts
(74) *Attorney, Agent, or Firm* — Westerman, Hattori, Daniels & Adrian, LLP

(57) ABSTRACT

The invention relates to a multilayer superoleophobic and/or superhydrophobic material comprising: • on the one hand, a first constituent that is a conductive substrate or a substrate that has previously been rendered conductive (1): • the surface of which is modified by chemical and/or physical treatment (2) and that incorporates a first adhesion-promoting conductive layer (3); • or that incorporates a first adhesion-promoting conductive layer (3); • and, on the other hand, at least one other constituent that is a superoleophobic and/or superhydrophobic polymer or copolymer layer (4, 5 or 6) composed of one or more monomers based on an aromatic or heteroaromatic ring substituted by one or more fluorocarbon and/or hydrocarbon chains. It is characterized in that the various constituents of said material comply with an increasing hydrophobicity gradient between the first layer deposited on the conductive substrate or substrate previously rendered conductive (1) and the last layer of said material.

20 Claims, 11 Drawing Sheets

(56) References Cited

U.S. PATENT DOCUMENTS

| | | | |
|---|---|---|---|
| 2009/0018249 | A1 | 1/2009 | Kanagasabapathy et al. |
| 2010/0069551 | A1 | 3/2010 | Minge et al. |
| 2010/0184346 | A1 | 7/2010 | Qi et al. |
| 2012/0164433 | A1 | 6/2012 | Advincula |
| 2012/0263922 | A1 | 10/2012 | Advincula et al. |

FOREIGN PATENT DOCUMENTS

| | | |
|---|---|---|
| EP | 2 210 921 A1 | 7/2010 |
| WO | 2007/102960 A2 | 9/2007 |
| WO | 2008/058895 A1 | 5/2008 |
| WO | 2008/106494 A1 | 9/2008 |
| WO | 2012/009238 A2 | 1/2012 |
| WO | 2012/075294 A2 | 6/2012 |

OTHER PUBLICATIONS

Wolfs et al., "Versatile Superhydrophobic Surfaces from a Bioinspired Approach", Macromolecules, vol. 44, No. 23, Dec. 13, 2011, pp. 9286-9294.

Liu et al., "Effect of Argon Plasma Treatment on Surface-Enhanced Raman Spectroscopy of Polypyrrole Deposited on Electrochemically Roughened Gold Substrates", J. Phys. Chem. B., vol. 109, No. 12, Mar. 2005, pp. 5779-5782.

Tuken et al., "The use of polythiophene for mild steel protection", Progress in Organic Coatings, vol. 51, No. 3, Dec. 2004, pp. 205-212.

Shustak et al., "n-Alkanoic Acid Monolayers on 316L Stainless Steel Promote the Adhesion of Electropolymerized Polypyrrole Films", Langmuir, vol. 22, No. 12, Jun. 2006, pp. 5237-5240.

Oberoi et al., "Synthesis of Specially Designed Adhesion Promoter for Grafting Polypyrrole", Macromolecular Symposia, vol. 254, No. 1, Aug. 2007, pp. 284-291.

Yang et al., "Modification of ITO Surface for High Performance of Electrochromic Polymer Film", ACTA CHIMICA SINICA, vol. 71, No. 7, May 2, 2013, pp. 1041-1046.

International Search Report dated Sep. 17, 2014, issued in corresponding application No. PCT/FR2014/000113 (3 pages).

Zenerino et al., "Connector Ability to Deisgn Superhydrophobic and Oleophobic Surfaces from Conducting Polymers", Langmuir, vol. 26, No. 16, Jul. 20, 2010, pp. 13545-13549.

\* cited by examiner

SUPEROLEOPHOBIC AND/OR SUPERHYDROPHOBIC MATERIAL, PROCESS FOR PREPARING SAME AND APPLICATIONS THEREOF

This invention relates to the development of a superoleophobic and/or superhydrophobic material. More specifically, the invention relates to a multilayer superoleophobic and/or superhydrophobic material including, on the one hand, a first constituent that is a conductive substrate or a substrate previously rendered conductive and, on the other hand, at least one other constituent that is a superoleophobic and/or superhydrophobic polymer or copolymer layer comprised of one or more monomers based on an aromatic or a heteroaromatic ring substituted by one or more fluorocarbon and/or hydrocarbon chains. It also relates to a process for preparing said material and its applications as an anti-corrosion, anti-adhesion and/or anti-friction material. The invention also relates to monomers, polymer or copolymer layers including said monomers and superoleophobic and/or superhydrophobic materials including said polymer or copolymer layers.

A material is defined as being superoleophobic or superhydrophobic when it has high-level anti-adhesive properties. Superhydrophobic materials are characterized in that a deposited liquid probe, water, will form an angle of contact at least greater than 140° or even greater than 150°. Among the superhydrophobic surfaces are sliding surfaces (low hysteresis) or non-sliding (high hysteresis). The lotus leaf perfectly illustrates a sliding superhydrophobic surface. In fact, on lotus leaves, which have both a double micro-nanometric structure and the presence of intrinsically hydrophobic materials (waxes) at the outermost surface, water runs off without wetting them. This phenomenon has moreover been referred to as the "lotus effect". Superoleophobic materials are characterized by the fact that a deposited liquid probe, of the oil type, may form an angle of contact at least greater than 130°, according to the type of oil used. In fact, different oils may be used to characterize the superoleophobicity and, in our case, oils or alkanes will be chosen having a surface tension ($\gamma_{LV}$) of less than or equal to 35 mN/m. As non-limiting examples of oils, it is possible to cite sunflower oil, rapeseed oil, or engine oil. As non-limiting examples of alkane, it is possible to cite hexadecane, dodecane, decane and octane.

Methods for producing superoleophobic surfaces using monomers containing perfluorinated chains are known from the document entitled "*Connector ability to design superhydrophobic and oleophobic surfaces from conducting polymers*", Langmuir, 26(16):13545-9, Zenerino A, Darmanin T, Taffin de Givenchy E, Amigoni S and Guittard F.

The application EP2210921 also describes articles including superhydrophobic coatings. The hydrophobic substance is made of polymers comprised of monomers such as, for example, ethylene, propylene, styrene or tetrafluoroethylene.

The application EP2118189 describes super- or ultra-hydrophobic compositions including polymers having a water contact angle (WCA) of between at least 120° and 150° or more.

The application US2008015298 describes superhydrophobic coatings made of fluorinated polymers having structural units of formula —$CR^1R^2$—CFX— and articles covered with such coatings, as well as the possible associated applications.

The international application WO2007102960 describes self-cleaning hydrophobic compositions in the form of films, and applications thereof.

The applications WO2012075294 and WO2012009238 describe superhydrophobic materials comprised of polymers or copolymers based on a substituted aromatic ring.

Finally, the application EP2092026 discloses ultra-hydrophobic coatings based on organosilicone copolymers.

However, the coatings or superoleophobic or superhydrophobic materials known at present are unstable, i.e. they adhere poorly to their substrate. Their superoleophobic or superhydrophobic properties are therefore relatively ephemeral. The coatings must therefore be replaced frequently, which in particular leads to pollution associated with the waste produced, requiring sustained maintenance and involving significant costs.

In addition, the superoleophobic or superhydrophobic materials or coatings as described in the above documents are also relatively complex to develop, i.e. they require multiple production steps. This therefore makes them relatively expensive to implement. Similarly, their difficult development generally requires the use of products, monomers, polymers, in particular fluorinated and containing perfluorinated chains, which are highly toxic, in particular in terms of bioaccumulation and environmental ecotoxicity.

There is therefore a need to obtain superoleophobic or superhydrophobic materials that have improved stability, i.e. that have a high power of adhesion to their substrate, in which the production process is advantageously inexpensive and preferably capable of being performed in a single step according to certain embodiments, advantageously with a favorable ecotoxic approach.

In addition, one objective associated with this invention is to provide superoleophobic or superhydrophobic materials having anti-adhesion, anti-friction and/or anti-corrosion properties that are stable, i.e. of which the polymer or copolymer layers adhere to their substrate.

In addition, the materials according to the invention may advantageously be used to form biomimetic or bionic surfaces, i.e. artificially reproducing essential properties of one or more process or biological surface.

Finally, the materials according to the invention or the surfaces including these materials are developed by an inexpensive process and in a single step. Thus, this technology may be applied in particular in the field of anti-bioadhesion, enabling the use of biocide on surfaces to be avoided, and thus new materials having high performance with a favorable ecotoxic approach to be designed.

The invention therefore has, as a first object, a multilayer superoleophobic and/or superhydrophobic material, including:

a first constituent that is a conductive substrate or a substrate previously rendered conductive:
  the surface of which is modified by a chemical and/or physical treatment;
  and/or
  integrating a first adhesion-promoting conductive layer;
and at least one other constituent that is a superoleophobic and/or superhydrophobic polymer or copolymer layer comprised of one or more monomers based on an aromatic or heteroaromatic ring substituted by one or more fluorocarbon and/or hydrocarbon chains,
characterized in that the different constituents of said material follow an increasing hydrophobicity gradient between the first layer deposited on the conductive substrate or a substrate previously rendered conductive and the last layer of said material.

It has, as a second object, a process for producing a superoleophobic and/or superhydrophobic material according to the invention, including the steps of:

physical and/or chemical treatment 2 of a conductive substrate or a substrate previously rendered conductive 1 and/or deposition of an adhesion-promoting conductive layer 3 on said substrate;

deposition on the adhesion-promoting conductive layer 3 of at least one superoleophobic and/or superhydrophobic polymer or copolymer layer 4, 5 or 6 comprised of one or more monomers based on an aromatic or heteroaromatic ring substituted by one or more fluorocarbon and/or hydrocarbon chains; and recovery of the superoleophobic and/or superhydrophobic material.

It has, as a third object, a fluorine-free monomer responding to the following general formula (I):

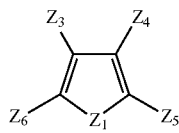

wherein:
$Z_1$ is chosen from the atoms and groups S, O, NH and N—W;
$Z_3$ is chosen from the atoms and groups H, $X_1$—W, $X_1$—$R_1$—$X_2$, $C(R_2)(R_3)$;
$Z_4$ is chosen from the atoms and groups W, $X_1$—W, $X_1$—$R_1$—$X_2$, $C(R_2)(R_3)$;
$Z_5$ and $Z_6$ represent an H atom or a hydrocarbon chain including 3 carbon atoms;
wherein:
W represents $B_1$—H, $Q_1$-$Z_2$ or $B_1$-$Q_1$-$Z_2$;
  with $B_1$, $B_2$, $B_3$, identical or different, chosen from the groups: $C_1$-$C_{20}$ alkyls, $C_1$-$C_{20}$ alkenyls, $C_1$-$C_{20}$ alkynyls, $C_6$-$C_{18}$ aryls, $C_6$-$C_{18}$ heteroaryls;
  with $Z_2$ corresponding to $A_1$, $CH(A_1)(A_2)$, $CH_2(A_1)$, $NH(A_1)$, $N(A_1)(A_2)$, $O(A_1)$ or $S(A_1)$;
for which $A_1$ and $A_2$, identical or different, represent:
$B_2$—H,
$B_3$-ph-$Q_2$-$B_2$—H; "ph" designating the functional phenyl group;
  with $Q_1$ and $Q_2$, identical or different, which represent OC(O), C(O), SC(O), NHC(O);
$X_1$ and $X_2$; identical or different, are chosen from the atoms or groups O, S, NH;
$R_1$ is chosen from the groups —CH(W)—, —$(CH_2)_{n1}$—CH(W)—, —CH(W)—$(CH_2)_{n1}$, —$(CH_2)_{n2}$—CH(W)—$(CH_2)_{n3}$— and
—$(CH_2)_{n1}$, when $Z_1$ equals N—W; W being as defined above and $n_1$, $n_2$, $n_3$, identical or different, are between 1 and 12, the sum of $n_2+n_3$ being less than or equal to 12;
$R_2$ is a hydrocarbon chain including 3 carbon atoms;
$R_3$ is chosen from the groups W, $X_1$—W or $X_1$—$R_1$—$X_2$;
and wherein:
when $Z_3$ and $Z_4$ correspond to $X_1$—$R_1$—$X_2$, they are linked to one another to form a ring;
when $Z_3$ and/or $Z_4$ correspond to $C(R_2)(R_3)$, they are linked to $Z_6$ and $Z_5$, ($Z_6$ and $Z_3$) and ($Z_5$ and $Z_4$), in order to form a 6-carbon aromatic ring, and when $R_3$ corresponds to $X_1$—$R_1$—$X_2$ then $Z_3$ and $Z_4$ are linked to one another and also form a ring;
and wherein, when $Z_1$ is an S atom:
if $Z_3$ is an H atom, then $Z_4$ is chosen from the groups $X_1$—W or $C(R_2)(R_3)$;

$Z_3$ and $Z_4$ cannot simultaneously be equal to OW;
and wherein, when $Z_1$ is an S or NW atom:
if $Z_3$ and $Z_4$ correspond to $X_1$—$R_1$—$X_2$, $n_1$ is equal to 1 and $Z_2$ corresponds to $CH_2(A_1)$ then $B_2$, $B_3$, identical or different, are chosen from the groups: $C_1$-$C_{20}$ alkenyls, $C_1$-$C_{20}$ alkynyls, $C_6$-$C_{18}$ aryls, $C_6$-$C_{18}$ heteroaryls;
and wherein, when $Z_1$ is N—W and W corresponds to $B_1$—H, then $B_1$ is chosen from the groups: $C_1$-$C_{20}$ alkenyls, $C_1$-$C_{20}$ alkynyls, $C_6$-$C_{18}$ aryls, $C_6$-$C_{18}$ heteroaryls.

It has, as a fourth object, a short-chain fluorinated monomer of formula (I) wherein:
$Z_1$ is chosen from the atoms and groups S, O, NH and N—W;
$Z_3$ is chosen from the atoms and groups H, $X_1$—W, $X_1$—$R_1$—$X_2$, $C(R_2)(R_3)$;
$Z_4$ is chosen from the atoms and groups W, $X_1$—W, $X_1$—$R_1$—$X_2$, $C(R_2)(R_3)$;
$Z_5$ and $Z_6$ represent an H atom or a hydrocarbon chain including 3 carbon atoms;
wherein:
W represents $(CF_2)_qF$, $B_1$—$(CF_2)_pF$, $Q_1$-$Z_2$ or $B_1$-$Q_1$-$Z_2$;
  with $B_1$, $B_2$, $B_3$, identical or different, chosen from the groups: $C_1$-$C_{20}$ alkyls, $C_1$-$C_{20}$ alkenyls, $C_1$-$C_{20}$ alkynyls, $C_6$-$C_{18}$ aryls, $C_6$-$C_{18}$ heteroaryls;
  with $Z_2$ corresponding to $A_1$, $CH(A_1)(A_2)$, $CH_2(A_1)$, $NH(A_1)$, $N(A_1)(A_2)$, $O(A_1)$ or $S(A_1)$;
for which $A_1$ and $A_2$, identical or different, represent:
—$B_2$—$(CF_2)_pF$,
—$B_3$-ph-$Q_2$-$B_2$—$(CF_2)_pF$; "ph" designating the functional phenyl group;
  with q and p being between 1 and 6;
  with $Q_1$ and $Q_2$, identical or different, which represent OC(O), C(O), SC(O), NHC(O);
$X_1$ and $X_2$, identical or different, are chosen from the atoms or groups O, S, NH;
$R_1$ is chosen from the groups —CH(W)—, —$(CH_2)_{n1}$—CH(W)—, —CH(W)—$(CH_2)_{n1}$, —$(CH_2)_{n2}$—CH(W)—$(CH_2)_{n3}$— and
—$(CH_2)_{n1}$, when $Z_1$ equals N—W; W being as defined above and $n_1$, $n_2$, $n_3$, identical or different, are between 1 and 12, the sum of $n_2+n_3$ being less than or equal to 12;
$R_2$ is a hydrocarbon chain including 3 carbon atoms;
$R_3$ is chosen from the groups W, $X_1$—W or $X_1$—$R_1$—$X_2$;
and wherein:
when $Z_3$ and $Z_4$ correspond to $X_1$—$R_1$—$X_2$, they are linked to one another to form a ring;
when $Z_3$ and/or $Z_4$ correspond to $C(R_2)(R_3)$, they are linked to $Z_6$ and $Z_5$, ($Z_6$ and $Z_3$) and ($Z_5$ and $Z_4$), in order to form a 6-carbon aromatic ring, and when $R_3$ corresponds to $X_1$—$R_1$—$X_2$ then $Z_3$ and $Z_4$ are linked to one another and also form a ring;
and wherein, when $Z_1$ is an S atom or an NH group:
if $Z_3$ is an H atom, then $Z_4$ is chosen from the groups $X_1$—W or $C(R_2)(R_3)$;
and wherein, when $Z_1$ is an S atom or the N—W group:
if $Z_3$ and $Z_4$ correspond to $X_1$—$R_1$—$X_2$, $n_1$ is equal to 1 while $Q_1$ is chosen from C(O) and NHC(O) so that $Z_2$ corresponds to $A_1$, $CH(A_1)(A_2)$, $CH_2(A_1)$, $NH(A_1)$, $N(A_1)(A_2)$ or $S(A_1)$.

It has, as a fifth object, a superoleophobic and/or superhydrophobic polymer or copolymer layer comprised of one or more fluorine-free monomers having a short fluorinated chain according to the invention.

It has, as a sixth object, a superoleophobic and/or superhydrophobic material including, on the one hand, a first constituent that is a conductive substrate or a substrate previously rendered conductive 1:
  the surface of which is modified by a chemical and/or physical treatment;
  and/or
  integrating a first adhesion-promoting conductive layer;
  and on the other hand at least one polymer or copolymer layer comprised of one or more monomers without fluorine or with a short fluorinated chain according to the invention.

Finally, it has, as a seventh object, the use of a material according to the invention as an anti-adhesion, anti-friction and/or anti-corrosion material.

The invention will be easier to understand in view of the following non-limiting description, drafted in view of the appended drawings, wherein.

Figure 10:
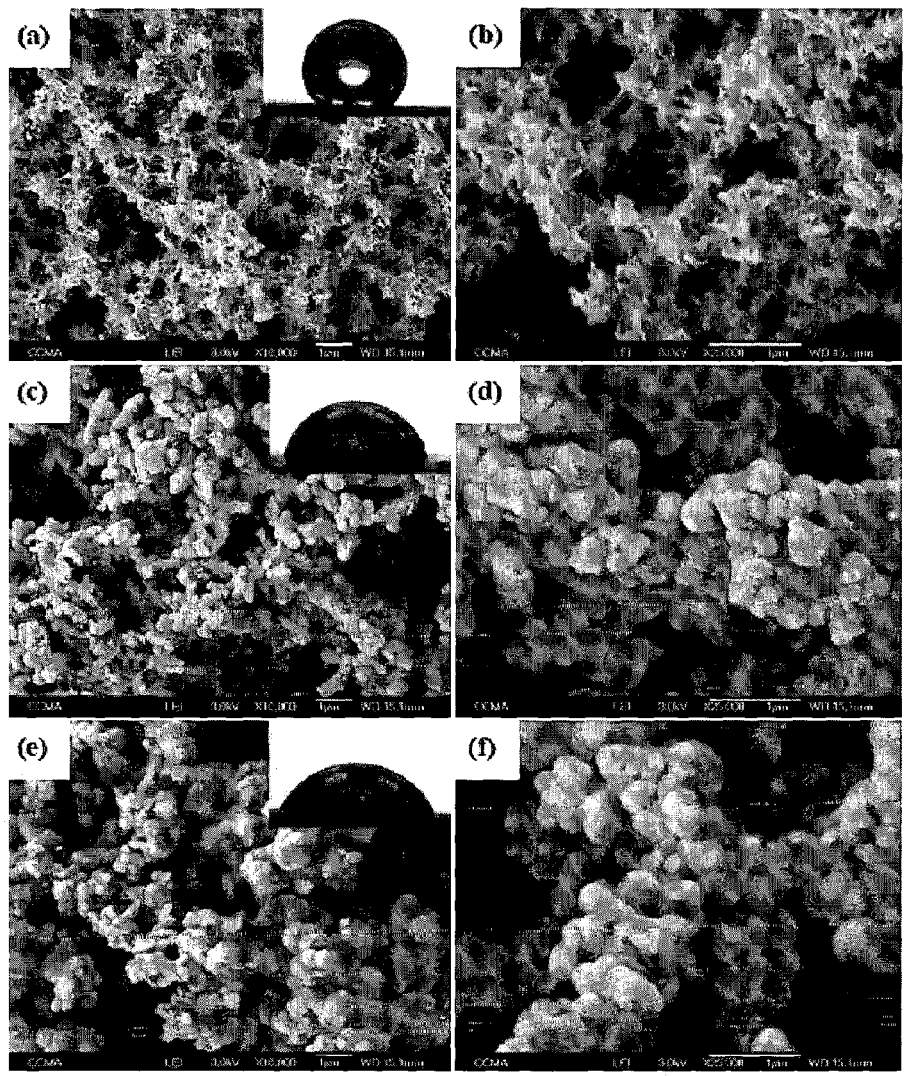
Figure 11A:
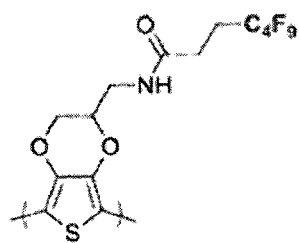
Figure 11A:
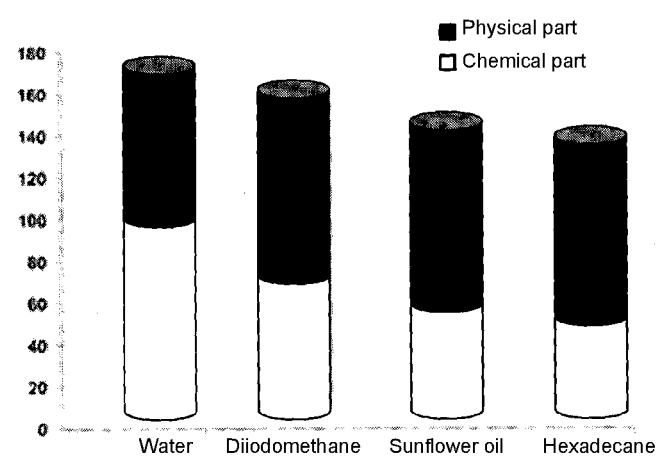
Figure 11A:
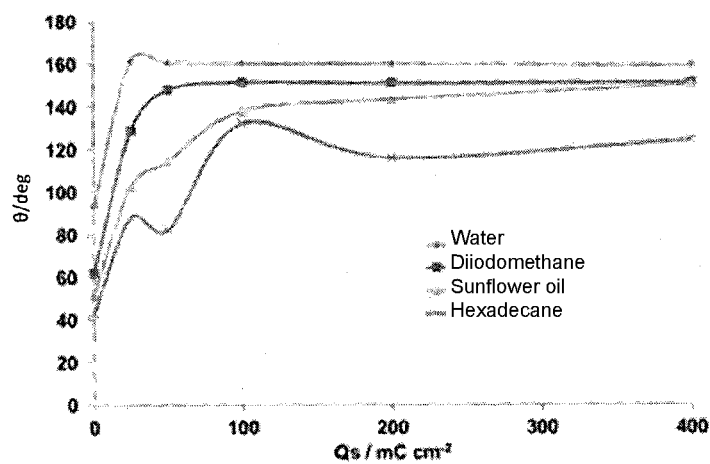
Figure 11B:
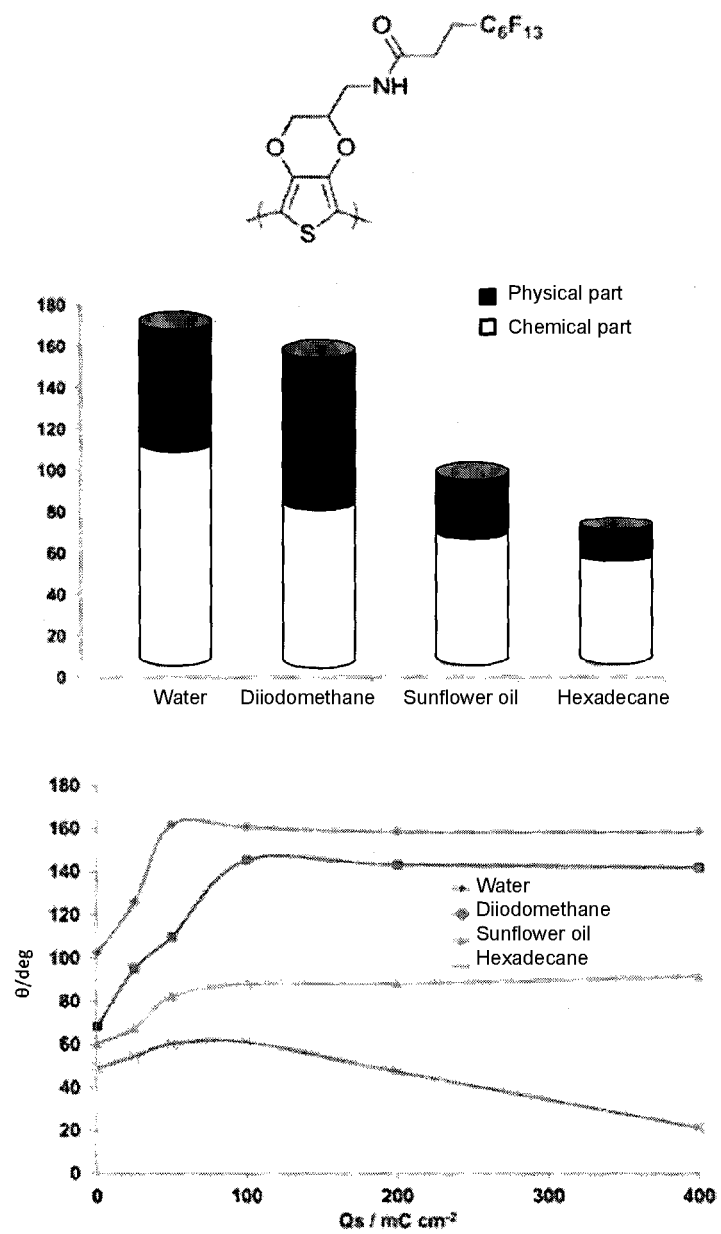
Figure 11C:
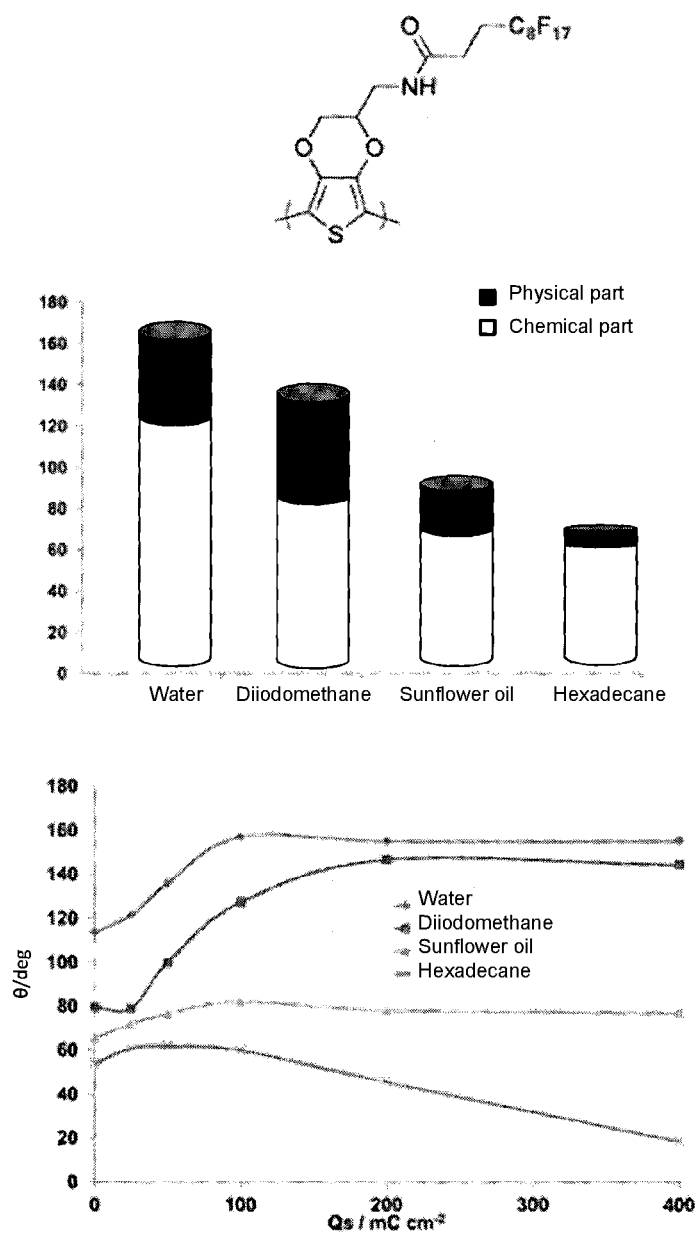
Figure 12:
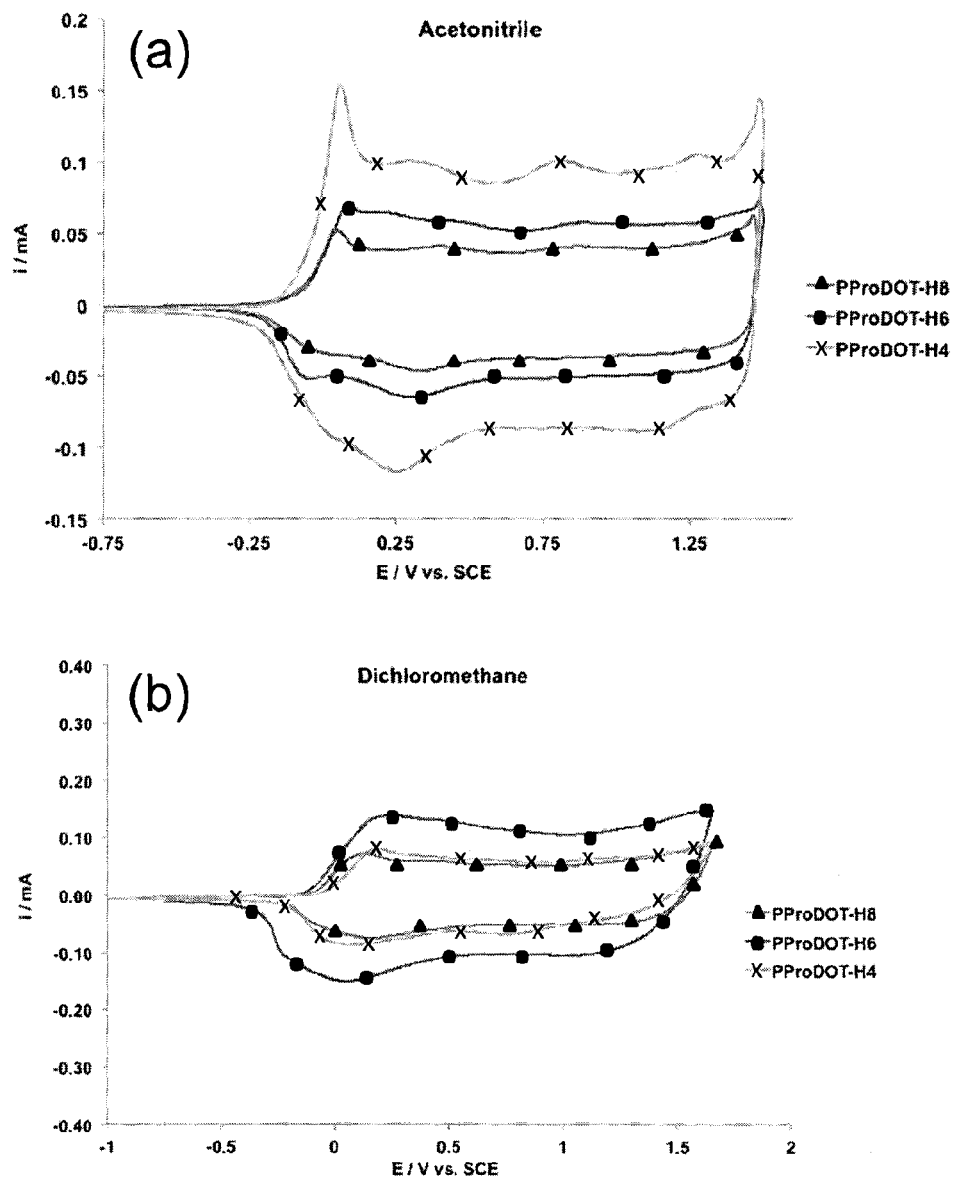
Figure 13:
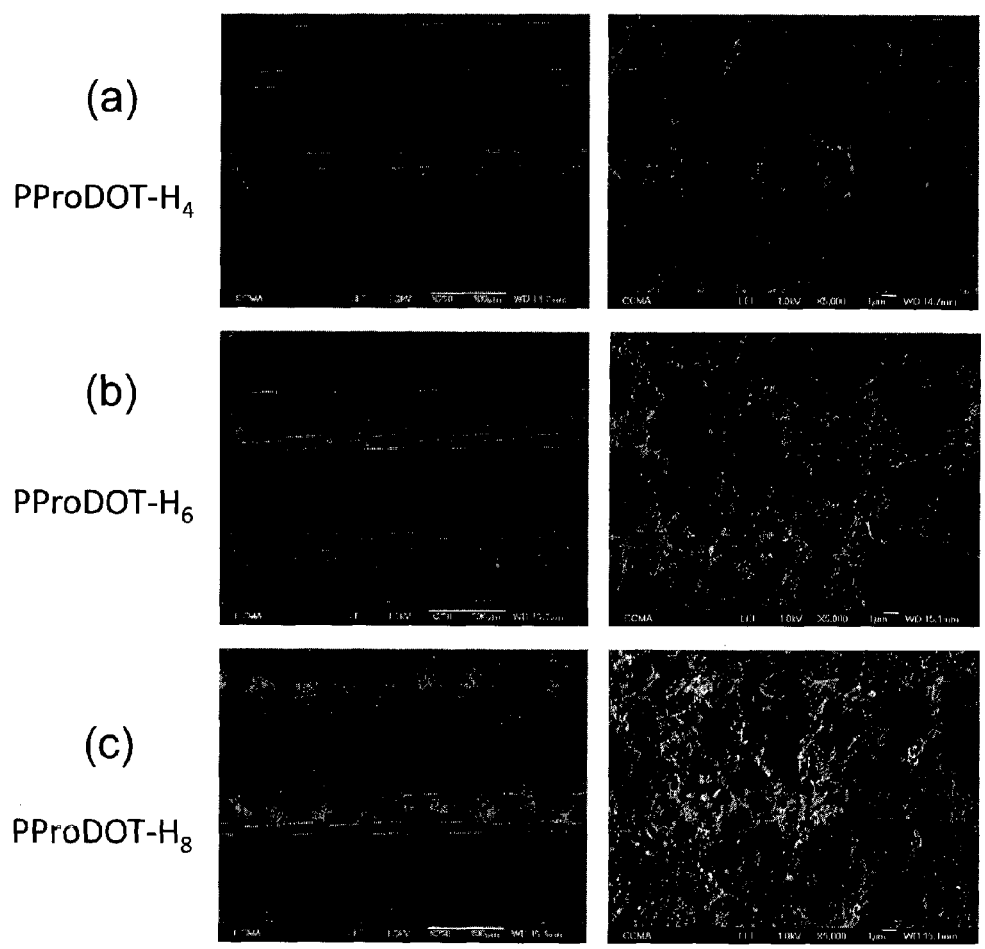
Figure 14:
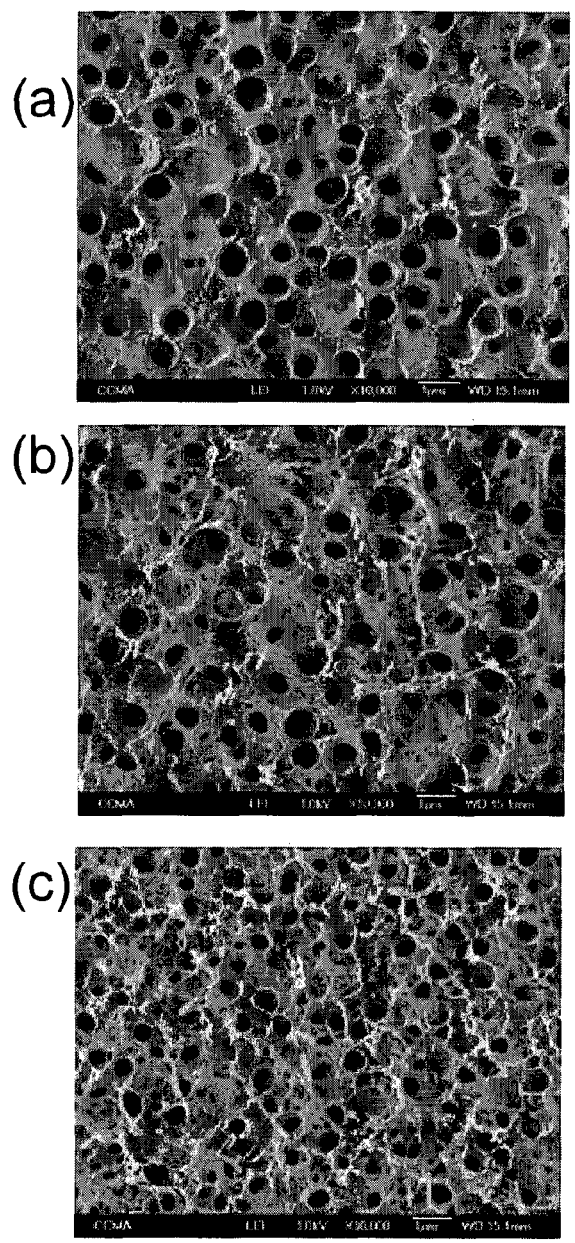

FIGS. 4 to 9 schematically show examples of embodiments of materials according to the invention;

FIG. 10 shows images, numbered 10(a) through 10(f), taken with a scanning electron microscope (SEM) with an enlargement of ×10,000 and ×25,000 of (a, b) PEDOT-NH-F4, (c, d) PEDOT-NH-F6 and (e, f) PEDOT-NH-F8. The inserts in FIGS. 10(a), 10(c) and 10(e) show hexadecane droplets on the surfaces;

FIGS. 11(a), 11(b) and 11(c) are schematic representations of the chemical part and the physical part of the angles of contact and influence of the deposition charge (Qs) on the contact angles. This data is presented for three polymers and four liquid probes (water, sunflower oil, diiodomethane and hexadecane);

FIG. 12 shows cyclic voltammograms of PProDOT-Hn (n=4, 6 or 8) in acetonitrile (a) and in dichloromethane (b);

FIG. 13 shows images taken with the scanning electron microscope (SEM) of PProDOT-$H_n$ polymers electrodeposited in acetonitrile. Image (a) concerns PProDOT-$H_4$, (b) concerns PProDOT-$H_6$ and (c) concerns PProDOT-$H_8$;

FIG. 14 shows images taken with the scanning electron microscope (SEM) of PProDOT-$H_n$ polymers electrodeposited in dichloromethane. Image (a) concerns PProDOT-$H_4$, (b) concerns PProDOT-$H_6$ and (c) concerns PProDOT-$H_8$.

The material according to the invention is a superoleophobic and/or superhydrophobic material including:
  a first constituent that is conductive or previously rendered conductive 1:
    the surface of which is modified by a chemical and/or physical treatment 2;
    and/or
    integrating a first adhesion-promoting conductive layer 3;
  and at least one other constituent that is a superoleophobic and/or superhydrophobic polymer or copolymer layer 4, 5 or 6 comprised of one or more monomers based on an aromatic or heteroaromatic ring substituted by one or more fluorocarbon and/or hydrocarbon chains.

The material according to the invention is characterized in that the different constituents of said material follow an increasing hydrophobicity gradient between the first layer deposited on the conductive substrate or a substrate previously rendered conductive and the last layer of said material.

As a non-limiting example, the conductive substrate or a substrate previously rendered conductive 1 may in particular be a steel (stainless or non-stainless), platinum, gold, silver, iron, indium and tin oxide (ITO), titanium, vitreous carbon, silicon, aluminum, copper, zinc, nickel, brass, bronze.

To increase the adhesion of the material according to the invention, the surface of the conductive substrate or a substrate previously rendered conductive 1 is modified:
  by physical and/or chemical treatments 2, without supplying material; and/or
  by deposition of an adhesion-promoting conductive layer 3, with a supply of material, which has the effect of modifying the chemistry of the surface.

The physical treatment of the surface of the conductive substrate or a substrate previously rendered conductive 1 may in particular be performed by plasma etching. Preferably, the physical treatment is performed by oxygen plasma or argon plasma.

The chemical treatment of the surface of the conductive substrate or a substrate previously rendered conductive 1 may in particular be performed by polishing, sanding, brushing and/or by a chemical attack. Advantageously, the chemical treatment is performed with *aqua regia*, which is a mixture of hydrochloric acid and nitric acid concentrated in a proportion of 2 to 4 volumes of hydrochloric acid for 1 volume of nitric acid.

The adhesion-promoting conductive layer 3 may be deposited according to a plurality of techniques: self-assembled monolayer (SAM), plasma, sol-gel, electrospinning, lithography, free radical polymerization, electrodeposition, layer-by-layer, dip-coating, or spin coating.

Advantageously, the self-assembled monolayer SAM includes undecylenic acid, undecanoic acid, decanoic acid, linoleic acid, octadecyl phosphonic acid, pyrrole undecanethiol, N-(3,4-dihydroxyphenethyl)thiophene-3-carboxamide, dopamine, taken alone or as a mixture.

Advantageously, the electrodeposition layer is comprised of one or more monomers based on an aromatic or heteroaromatic ring, optionally substituted. Preferably, the electrodeposition layer is comprised of one or more pyrrole or aniline monomers, taken alone or as a mixture.

Preferably, the electrodeposition layer is comprised of polypyrrole monomers:

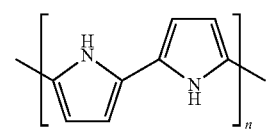

Surprisingly, the applicant was able to demonstrate that the thickness of the conductive layer 3 played a critical role on its adhesion to the conductive substrate or a substrate previously rendered conductive 1. In fact, the applicant established that cohesion was inversely proportional to the thickness of the deposited layer. Thus, the adhesion-promoting conductive layer preferably has a thickness of less than 100 nm. More preferably, the thickness is between 1 and 50 nm, and even more preferably 20 nm. This thickness is dependent on the surface charge applied, which is preferably between 1 and 20 mC/cm$^2$. Preferably, the surface charge is 5 mC/cm$^2$.

The applicant was able to demonstrate that, even if the conductive layer is fine, it prevents a cohesive rupture. In addition, it could be established that the thickness of the polypyrrole influences the wettability properties of the superhydrophobic polymer. The greater the thickness of the polypyrrole is, the smaller the contact angle of the superhydrophobic polymer will be. The multilayer material according to the invention also includes at least one other constituent, which is a superoleophobic and/or superhydrophobic polymer or copolymer layer 4, 5 or 6 comprised of one or more monomers based on an aromatic or heteroaromatic ring, substituted by one or more fluorocarbon and/or hydrocarbon chains.

Preferably, the superoleophobic and/or superhydrophobic polymer or copolymer layer 4, 5 or 6 is comprised of one or more monomers responding to the following general formula:

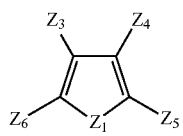

(I)

wherein:
$Z_1$ is chosen from the atoms and groups S, O, NH and N—W;
$Z_3$ is chosen from the atoms and groups H, $X_1$—W, $X_1$—$R_1$—$X_2$, C($R_2$)($R_3$);
$Z_4$ is chosen from the groups W, $X_1$—W, $X_1$—$R_1$—$X_2$, C($R_2$) ($R_3$);
$Z_5$ and $Z_6$ represent an H atom or a hydrocarbon chain including 3 carbon atoms;
wherein:
W represents $(CF_2)_qF$, $B_1$—$(CY_2)_pY$, $Q_1$-$Z_2$ or $B_1$-$Q_1$-$Z_2$;
  with $B_1$, $B_2$, $B_3$, identical or different, chosen from the groups: $C_1$-$C_{20}$ alkyls, $C_1$-$C_{20}$ alkenyls, $C_1$-$C_{20}$ alkynyls, $C_6$-$C_{18}$ aryls, $C_6$-$C_{18}$ heteroaryls;
  with $Z_2$ corresponding to $A_1$, CH($A_1$)($A_2$), $CH_2$($A_1$), NH($A_1$), N($A_1$)($A_2$), O($A_1$) or S($A_1$);
  for which $A_1$ and $A_2$, identical or different, represent:
  —$B_2$—$(CY_2)_pY$,
  —$B_3$-ph-$Q_2$-$B_2$—$(CY_2)_pY$; "ph" designating the functional phenyl group;
    with q being between 1 and 20 and p between 0 and 20;
    with Y corresponding to H or F, except when Y is an H atom, then p is equal to 0;
    with $Q_1$ and $Q_2$, identical or different, which represent OC(O), C(O), SC(O), NHC(O);
$X_1$ and $X_2$; identical or different, are chosen from the atoms or groups O, S, NH;
$R_1$ is chosen from the groups —CH(W)—, —$(CH_2)_{n1}$—CH(W)—, —CH(W)—$(CH_2)_{n1}$, —$(CH_2)_{n2}$—CH(W)—$(CH_2)_{n3}$— and —$(CH_2)_{n1}$, when $Z_1$ equals N—W; W being as defined above and $n_1$, $n_2$, $n_3$, identical or different, are between 1 and 12, the sum of $n_2$+$n_3$ being less than or equal to 12;
$R_2$ is a hydrocarbon chain including 3 carbon atoms;
$R_3$ is chosen from the groups W, $X_1$—W or $X_1$—$R_1$—$X_2$;
and wherein:
when $Z_3$ and $Z_4$ correspond to $X_1$—$R_1$—$X_2$, they are linked to one another to form a ring;
when $Z_3$ and/or $Z_4$ correspond to C($R_2$)($R_3$), they are linked to $Z_6$ and $Z_5$, ($Z_6$ and $Z_3$) and ($Z_5$ and $Z_4$), in order to form a 6-carbon aromatic ring, and when $R_3$ corresponds to $X_1$—$R_1$—$X_2$ then $Z_3$ and $Z_4$ are linked to one another and also form a ring;
taken together or as a mixture.

Also preferably, the superoleophobic and/or superhydrophobic polymer or copolymer layer 4, 5 or 6 according to the invention is comprised of one or more monomers responding to the general formula (I), wherein:
$Z_1$ is chosen from the atoms and groups S, NH and N—W;
$Z_3$ is chosen from the atoms and groups H, $X_1$—W, $X_1$—$R_1$—$X_2$;
$Z_4$ is chosen from the atoms and groups W, $X_1$—W, $X_1$—$R_1$—$X_2$;
$Z_5$ and $Z_6$ represent an H atom;
wherein:
W represents $(CF_2)_qF$, $B_1$—$(CY_2)_pY$, $Q_1$-$Z_2$ or $B_1$-$Q_1$-$Z_2$;
  with $B_1$, $B_2$, $B_3$, identical or different, chosen from the groups: $C_1$-$C_{16}$ alkyls, $C_1$-$C_{16}$ alkenyls, $C_1$-$C_{16}$ alkynyls, $C_6$-$C_{18}$ aryls, $C_6$-$C_{18}$ heteroaryls;
  with $Z_2$ corresponding to $A_1$, CH($A_1$)($A_2$), $CH_2$($A_1$), NH($A_1$), N($A_1$)($A_2$), O($A_1$) or S($A_1$);
  for which $A_1$ and $A_2$, identical or different, represent:
  —$B_2$—$(CY_2)_pY$,
  —$B_3$-ph-$Q_2$-$B_2$—$(CY_2)_pY$; "ph" designating the functional phenyl group;
    with q being between 1 and 16 and p being between 0 and 16;
    with Y corresponding to H or F, except when Y is an H atom, then p is equal to 0;
    with $Q_1$ and $Q_2$, identical or different, which represent OC(O), C(O), SC(O), NHC(O);
$X_1$ and $X_2$, identical or different, are chosen from the atoms or groups O, S;
$R_1$ is chosen from the groups —CH(W)—, —$(CH_2)_{n1}$—CH(W)—, —CH(W)—$(CH_2)_{n1}$, —$(CH_2)_{n2}$—CH(W)—$(CH_2)_{n3}$— and —$(CH_2)_{n1}$— when $Z_1$ equals N—W; W being as defined above and $n_1$, $n_2$, $n_3$, identical or different, are between 1 and 4, the sum of $n_2$+$n_3$ being less than or equal to 4;
and wherein:
when $Z_3$ and $Z_4$ correspond to $X_1$—$R_1$—$X_2$, they are linked to one another to form a ring;
taken alone or as a mixture.

The superoleophobic and/or superhydrophobic polymer or copolymer layer 4, 5 or 6 according to the invention is preferably comprised of one or more monomers chosen from:
(i) the compounds of formula (I) wherein:
$Z_1$ is chosen from the atoms and groups S, NH and N—W;
$Z_3$ is chosen from the atoms and groups H, $X_1$—W, $X_1$—$R_1$—$X_2$;
$Z_4$ is chosen from the atoms and groups W, $X_1$—W, $X_1$—$R_1$—$X_2$;
$Z_5$ and $Z_6$ represent an H atom;
wherein:
W represents $(CF_2)_qF$, $B_1$—$(CF_2)_pF$, $Q_1$-$Z_2$ or $B_1$-$Q_1$-$Z_2$;
  with $B_1$, $B_2$, $B_3$, identical or different, chosen from the groups: $C_1$-$C_{16}$ alkyls, $C_1$-$C_{16}$ alkenyls, $C_1$-$C_{16}$ alkynyls, $C_6$-$C_{18}$ aryls, $C_6$-$C_{18}$ heteroaryls;
  with $Z_2$ corresponding to $A_1$, CH($A_1$)($A_2$), $CH_2$($A_1$), NH($A_1$), N($A_1$)($A_2$), O($A_1$) or S($A_1$);
  for which $A_1$ and $A_2$, identical or different, represent:
  —$B_2$—$(CF_2)_pF$,
  —$B_3$-ph-$Q_2$-$B_2$—$(CF_2)_pF$; "ph" designating the functional phenyl group;
    with q and p being between 7 and 16;
    with $Q_1$ and $Q_2$, identical or different, which represent OC(O), C(O), SC(O), NHC(O);
$X_1$ and $X_2$, identical or different, are chosen from the atoms or groups O, S;

$R_1$ is chosen from the groups —CH(W)—, —$(CH_2)_{n1}$—CH(W)—, —CH(W)—$(CH_2)_{n1}$, —$(CH_2)_{n2}$—CH(W)—$(CH_2)_{n3}$— and —$(CH_2)_{n1}$— when $Z_1$ equals N—W; W being as defined above and $n_1$, $n_2$, $n_3$, identical or different, are between 1 and 4, the sum of $n_2+n_3$ being less than or equal to 4;

and wherein:

when $Z_3$ and $Z_4$ correspond to $X_1$—$R_1$—$X_2$, they are linked to one another to form a ring;

or from (ii) the following fluorine-free compounds, also responding to the general formula (I) wherein:

$Z_1$ is chosen from the atoms and groups S, O, NH and N—W;

$Z_3$ is chosen from the atoms and groups H, $X_1$—W, $X_1$—$R_1$—$X_2$, $C(R_2)(R_3)$;

$Z_4$ is chosen from the atoms and groups W, $X_1$—W, $X_1$—$R_1$—$X_2$, $C(R_2)(R_3)$;

$Z_5$ and $Z_6$ represent an H atom or a hydrocarbon chain including 3 carbon atoms;

wherein:

W represents $B_1$—H, $Q_1$-$Z_2$ or $B_1$-$Q_1$-$Z_2$;

with $B_1$, $B_2$, $B_3$, identical or different, chosen from the groups: $C_1$-$C_{20}$ alkyls, $C_1$-$C_{20}$ alkenyls, $C_1$-$C_{20}$ alkynyls, $C_6$-$C_{18}$ aryls, $C_6$-$C_{18}$ heteroaryls;

with $Z_2$ corresponding to $A_1$, $CH(A_1)(A_2)$, $CH_2(A_1)$, $NH(A_1)$, $N(A_1)(A_2)$, $O(A_1)$ or $S(A_1)$;

for which $A_1$ and $A_2$, identical or different, represent:

—$B_2$—H,

—$B_3$-ph-$Q_2$-$B_2$—H; "ph" designating the functional phenyl group;

with $Q_1$ and $Q_2$, identical or different, which represent OC(O), C(O), SC(O), NHC(O);

$X_1$ and $X_2$, identical or different, are chosen from the atoms or groups O, S, NH;

$R_1$ is chosen from the groups —CH(W)—, —$(CH_2)_{n1}$—CH(W)—, —CH(W)—$(CH_2)_{n1}$, —$(CH_2)_{n2}$—CH(W)—$(CH_2)_{n3}$—; and —$(CH_2)_{n1}$— when $Z_1$ equals N—W; W being as defined above and $n_1$, $n_2$, $n_3$, identical or different, are between 1 and 12, the sum of $n_2+n_3$ being less than or equal to 12;

$R_2$ is a hydrocarbon chain including 3 carbon atoms;

$R_3$ is chosen from the groups W, $X_1$—W or $X_1$—$R_1$—$X_2$;

and wherein:

when $Z_3$ and $Z_4$ correspond to $X_1$—$R_1$—$X_2$, they are linked to one another to form a ring;

when $Z_3$ and/or $Z_4$ correspond to $C(R_2)(R_3)$, they are linked to $Z_6$ and $Z_5$, ($Z_6$ and $Z_3$) and ($Z_5$ and $Z_4$), to form a 6-carbon aromatic ring, and when $R_3$ corresponds to $X_1$—$R_1$—$X_2$, then $Z_3$ and $Z_4$ are linked to one another and also form a ring;

or from (iii) the following short-chain fluorinated compounds also responding to the general formula (I) wherein:

$Z_1$ is chosen from the atoms and groups S, O, NH and N—W;

$Z_3$ is chosen from the atoms and groups H, $X_1$—W, $X_1$—$R_1$—$X_2$, $C(R_2)(R_3)$;

$Z_4$ is chosen from the atoms and groups W, $X_1$—W, $X_1$—$R_1$—$X_2$, $C(R_2)(R_3)$;

$Z_5$ and $Z_6$ represent an H atom or a hydrocarbon chain including 3 carbon atoms;

wherein:

W represents $(CF_2)_qF$, $B_1$—$(CF_2)_pF$, $Q_1$-$Z_2$ or $B_1$-$Q_1$-$Z_2$;

with $B_1$, $B_2$, $B_3$, identical or different, chosen from the groups: $C_1$-$C_{20}$ alkyls, $C_1$-$C_{20}$ alkenyls, $C_1$-$C_{20}$ alkynyls, $C_6$-$C_{18}$ aryls, $C_6$-$C_{18}$ heteroaryls;

with $Z_2$ corresponding to $A_1$, $CH(A_1)(A_2)$, $CH_2(A_1)$, $NH(A_1)$, $N(A_1)(A_2)$, $O(A_1)$ or $S(A_1)$;

for which $A_1$ and $A_2$, identical or different, represent:

—$B_2$—$(CF_2)_pF$,

—$B_3$-ph-$Q_2$-$B_2$—$(CF_2)_pF$; "ph" designating the functional phenyl group;

with q and p being between 1 and 6;

with $Q_1$ and $Q_2$, identical or different, which represent OC(O), C(O), SC(O), NHC(O);

$X_1$ and $X_2$, identical or different, are chosen from the atoms or groups O, S, NH;

$R_1$ is chosen from the groups —CH(W)—, —$(CH_2)_{n1}$—CH(W)—, —CH(W)—$(CH_2)_{n1}$, —$(CH_2)_{n2}$—CH(W)—$(CH_2)_{n3}$—; and —$(CH_2)_{n1}$— when $Z_1$ equals N—W; W being as defined above and $n_1$, $n_2$, $n_3$, identical or different, are between 1 and 12, the sum of $n_2+n_3$ being less than or equal to 12;

$R_2$ is a hydrocarbon chain including 3 carbon atoms;

$R_3$ is chosen from the groups W, $X_1$—W or $X_1$—$R_1$—$X_2$;

and wherein:

when $Z_3$ and $Z_4$ correspond to $X_1$—$R_1$—$X_2$, they are linked to one another to form a ring;

when $Z_3$ and/or $Z_4$ correspond to $C(R_2)(R_3)$, they are linked to $Z_6$ and $Z_5$, ($Z_6$ and $Z_3$) and ($Z_5$ and $Z_4$), to form a 6-carbon aromatic ring, and when $R_3$ corresponds to $X_1$—$R_1$—$X_2$, then $Z_3$ and $Z_4$ are linked to one another and also form a ring;

taken alone or as a mixture.

Particularly advantageously, the superoleophobic and/or superhydrophobic polymer or copolymer layer 4, 5 or 6 according to the invention is comprised of one or more monomers chosen:

from the following fluorine-free compounds, responding to the following general formula (I), wherein:

$Z_1$ is chosen from the atoms and groups S, NH and N—W;

$Z_3$ is chosen from the atoms and groups H, $X_1$—W, $X_1$—$R_1$—$X_2$;

$Z_4$ is chosen from the atoms and groups W, $X_1$—W, $X_1$—$R_1$—$X_2$;

$Z_5$ and $Z_6$ represent an H atom;

wherein:

W represents $B_1$—H, $Q_1$-$Z_2$ or $B_1$-$Q_1$-$Z_2$;

with $B_1$, $B_2$, $B_3$, identical or different, chosen from the groups: $C_1$-$C_{16}$ alkyls, $C_1$-$C_{16}$ alkenyls, $C_1$-$C_{16}$ alkynyls, $C_6$-$C_{18}$ aryls, $C_6$-$C_{18}$ heteroaryls;

with $Z_2$ corresponding to $A_1$, $CH(A_1)(A_2)$, $CH_2(A_1)$, $NH(A_1)$, $N(A_1)(A_2)$, $O(A_1)$ or $S(A_1)$;

for which $A_1$ and $A_2$, identical or different, represent:

—$B_2$—H,

—$B_3$-ph-$Q_2$-$B_2$—H; "ph" designating the functional phenyl group;

with $Q_1$ and $Q_2$, identical or different, which represent OC(O), C(O), SC(O), NHC(O);

$X_1$ and $X_2$, identical or different, are chosen from the atoms or groups O, S;

$R_1$ is chosen from the groups —CH(W)—, —$(CH_2)_{n1}$—CH(W)—, —CH(W)—$(CH_2)_{n1}$, —$(CH_2)_{n2}$—CH(W)—$(CH_2)_{n3}$— and —$(CH_2)_{n1}$— when $Z_1$ equals N—W; W being as defined above and $n_1$, $n_2$, $n_3$, identical or different, are between 1 and 4, the sum of $n_2+n_3$ being less than or equal to 4;

and wherein:
when $Z_3$ and $Z_4$ correspond to $X_1$—$R_1$—$X_2$, they are linked to one another to form a ring;
or from the following short-chain fluorinated compounds also responding to the general formula (I), wherein:
$Z_1$ is chosen from the atoms and groups S, NH and N—W;
$Z_3$ is chosen from the atoms and groups H, $X_1$—W, $X_1$—$R_1$—$X_2$;
$Z_4$ is chosen from the atoms and groups W, $X_1$—W, $X_1$—$R_1$—$X_2$;
$Z_5$ and $Z_6$ represent an H atom;
wherein:
W represents $(CF_2)_4F$, $B_1$—$(CF_2)_4F$, $Q_1$-$Z_2$ or $B_1$-$Q_1$-$Z_2$;
with $B_1$, $B_2$, $B_3$, identical or different, chosen from the groups: $C_1$-$C_{14}$ alkyls;
with $Z_2$ corresponding to $A_1$, $CH(A_1)(A_2)$, $CH_2(A_1)$, $NH(A_1)$, $N(A_1)(A_2)$, $O(A_1)$ or $S(A_1)$;
for which $A_1$ and $A_2$, identical or different, represent:
—$B_2$—$(CF_2)_4F$,
—$B_3$-ph-$Q_2$-$B_2$—$(CF_2)_4F$; "ph" designating the functional phenyl group;
with $Q_1$ and $Q_2$, identical or different, which represent OC(O), C(O), SC(O), NHC(O);
$X_1$ and $X_2$, identical or different, are chosen from the atoms or groups O, S;
$R_1$ is chosen from the groups —CH(W)—, —$(CH_2)_{n1}$—CH(W)—, —CH(W)—$(CH_2)_{n1}$, —$(CH_2)_{n2}$—CH(W)—$(CH_2)_{n3}$— and —$(CH_2)_{n1}$-when $Z_1$ equals N—W; W being as defined above and $n_1$, $n_2$, $n_3$, identical or different, are between 1 and 4, the sum of $n_2+n_3$ being less than or equal to 4;
and wherein:
when $Z_3$ and $Z_4$ correspond to $X_1$—$R_1$—$X_2$, they are linked to one another to form a ring;
taken alone or as a mixture.

According to a first advantageous embodiment of the invention, the superoleophobic and/or superhydrophobic polymer or copolymer layer 4, 5 or 6 is comprised only of one or more fluorine-free monomers responding to general formula (I), wherein:
$Z_1$ is chosen from the atoms and groups S, O, NH and N—W;
$Z_3$ is chosen from the atoms and groups H, $X_1$—W, $X_1$—$R_1$—$X_2$, $C(R_2)(R_3)$;
$Z_4$ is chosen from the atoms and groups W, $X_1$—W, $X_1$—$R_1$—$X_2$, $C(R_2)(R_3)$;
$Z_5$ and $Z_6$ represent an H atom or a hydrocarbon chain including 3 carbon atoms;
wherein:
W represents $B_1$—H, $Q_1$-$Z_2$ or $B_1$-$Q_1$-$Z_2$;
with $B_1$, $B_2$, $B_3$, identical or different, chosen from the groups: $C_1$-$C_{20}$ alkyls, $C_1$-$C_{20}$ alkenyls, $C_1$-$C_{20}$ alkynyls, $C_6$-$C_{18}$ aryls, $C_6$-$C_{18}$ heteroaryls;
with $Z_2$ corresponding to $A_1$, $CH(A_1)(A_2)$, $CH_2(A_1)$, $NH(A_1)$, $N(A_1)(A_2)$, $O(A_1)$ or $S(A_1)$;
for which $A_1$ and $A_2$, identical or different, represent:
—$B_2$—H,
—$B_3$-ph-$Q_2$-$B_2$—H; "ph" designating the functional phenyl group;
with $Q_1$ and $Q_2$, identical or different, which represent OC(O), C(O), SC(O), NHC(O);
$X_1$ and $X_2$, identical or different, are chosen from the atoms or groups O, S, NH;
$R_1$ is chosen from the groups —CH(W)—, —$(CH_2)_{n1}$—CH(W)—, —CH(W)—$(CH_2)_{n1}$, —$(CH_2)_{n2}$—CH(W)—$(CH_2)_{n3}$—; and
—$(CH_2)_{n1}$— when $Z_1$ equals N—W; W being as defined above and $n_1$, $n_2$, $n_3$, identical or different, are between 1 and 12, the sum of $n_2+n_3$ being less than or equal to 12;
$R_2$ is a hydrocarbon chain including 3 carbon atoms;
$R_3$ is chosen from the groups W, $X_1$—W or $X_1$—$R_1$—$X_2$;
and wherein:
when $Z_3$ and $Z_4$ correspond to $X_1$—$R_1$—$X_2$, they are linked to one another to form a ring;
when $Z_3$ and/or $Z_4$ correspond to $C(R_2)(R_3)$, they are linked to $Z_6$ and $Z_5$, ($Z_6$ and $Z_3$) and ($Z_5$ and $Z_4$), to form a 6-carbon aromatic ring, and when $R_3$ corresponds to $X_1$—$R_1$—$X_2$, then $Z_3$ and $Z_4$ are linked to one another and also form a ring;
taken alone or as a mixture.

Preferably, according to this first advantageous embodiment, the superoleophobic and/or superhydrophobic polymer or copolymer layer 4, 5 or 6 is comprised only of one or more monomers responding to formula (II):

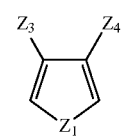

wherein:
$Z_1$ is chosen from the atoms and groups S, NH and N—W;
$Z_3$ and $Z_4$ represent $X_1$—$R_1$—$X_2$ and are linked to one another to form a ring:
$X_1$ and $X_2$ are chosen from the atoms and groups O, S;
$R_1$ is chosen from the following groups:
—$(CH_2)_{n1}$—CH(W)—,
—CH(W)—$(CH_2)_{n1}$,
—$(CH_2)_{n2}$—CH(W)—$(CH_2)_{n3}$;
W represents —$B_1$—H, $Q_1$-$Z_2$ or $B_1$-$Q_1$-$Z_2$, with $Z_2$ corresponding to $A_1$, $CH(A_1)(A_2)$, $CH_2(A_1)$, $NH(A_1)$, $N(A_1)(A_2)$, $O(A_1)$ or $S(A_1)$;
for which $A_1$ and $A_2$, identical or different, represent:
—$B_2$—H, with $B_1$, $B_2$, identical or different, chosen from the groups: $C_1$-$C_{16}$ alkyls, $C_1$-$C_{14}$ alkenyls, $C_1$-$C_{16}$ alkynyls, $C_6$-$C_{18}$ aryls, $C_6$-$C_{18}$ heteroaryls;
with $Q_1$ representing OC(O), C(O), SC(O), NHC(O), $n_1$, $n_2$, $n_3$, identical or different, are between 1 and 4, the sum of $n_2+n_3$ being less than or equal to 4;
taken alone or as a mixture.

According to a second advantageous embodiment of the invention, the superoleophobic and/or superhydrophobic polymer or copolymer layer 4, 5 or 6 is comprised only of one or more short-chain fluorinated monomers responding to general formula (I) wherein:
$Z_1$ is chosen from the atoms and groups S, O, NH and N—W;
$Z_3$ is chosen from the atoms and groups H, $X_1$—W, $X_1$—$R_1$—$X_2$, $C(R_2)(R_3)$;
$Z_4$ is chosen from the atoms and groups W, $X_1$—W, $X_1$—$R_1$—$X_2$, $C(R_2)(R_3)$;
$Z_5$ and $Z_6$ represent an H atom or a hydrocarbon chain including 3 carbon atoms;
wherein:
W represents $(CF_2)_qF$, $B_1$—$(CF_2)_pF$, $Q_1$-$Z_2$ or $B_1$-$Q_1$-$Z_2$;
with $B_1$, $B_2$, $B_3$, identical or different, chosen from the groups: $C_1$-$C_{20}$ alkyls, $C_1$-$C_{20}$ alkenyls, $C_1$-$C_{20}$ alkynyls, $C_6$-$C_{18}$ aryls, $C_6$-$C_{18}$ heteroaryls;

with $Z_2$ corresponding to $A_1$, $CH(A_1)(A_2)$, $CH_2(A_1)$, $NH(A_1)$, $N(A_1)(A_2)$, $O(A_1)$ or $S(A_1)$;

for which $A_1$ and $A_2$, identical or different, represent:
—$B_2$—$(CF_2)_pF$,
—$B_3$-ph-$Q_2$-$B_2$—$(CF_2)_pF$; "ph" designating the functional phenyl group;
with q and p being between 1 and 6;
with $Q_1$ and $Q_2$, identical or different, which represent $OC(O)$, $C(O)$, $SC(O)$, $NHC(O)$;

$X_1$ and $X_2$, identical or different, are chosen from the atoms or groups O, S, NH;

$R_1$ is chosen from the groups —$CH(W)$—, —$(CH_2)_{n1}$—$CH(W)$—, —$CH(W)$—$(CH_2)_{n1}$, —$(CH_2)_{n2}$—$CH(W)$—$(CH_2)_{n3}$—; and
—$(CH_2)_{n1}$— when $Z_1$ equals N—W; W being as defined above and $n_1$, $n_2$, $n_3$, identical or different, are between 1 and 12, the sum of $n_2+n_3$ being less than or equal to 12;

$R_2$ is a hydrocarbon chain including 3 carbon atoms;
$R_3$ is chosen from the groups W, $X_1$—W or $X_1$—$R_1$—$X_2$;
and wherein:
when $Z_3$ and $Z_4$ correspond to $X_1$—$R_1$—$X_2$, they are linked to one another to form a ring;
when $Z_3$ and/or $Z_4$ correspond to $C(R_2)$ $(R_3)$, they are linked to $Z_6$ and $Z_5$, ($Z_6$ and $Z_3$) and ($Z_5$ and $Z_4$), to form a 6-carbon aromatic ring, and when $R_3$ corresponds to $X_1$—$R_1$—$X_2$, then $Z_3$ and $Z_4$ are linked to one another and also form a ring;
taken alone or as a mixture.

Preferably, according to this second advantageous embodiment, the superoleophobic and/or superhydrophobic polymer or copolymer layer 4, 5 or 6 according to the invention is comprised only of one or more monomers responding to the following formula:

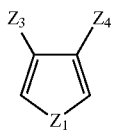

(II)

wherein:
$Z_1$ is chosen from the atoms and groups S, NH and N—W;
$Z_3$ and $Z_4$ represent $X_1$—$R_1$—$X_2$ and are linked to one another to form a ring;
$X_1$ and $X_2$ are chosen from the atoms and groups O, S;
$R_1$ is chosen from the following groups:
—$(CH_2)_{n1}$—$CH(W)$—,
—$CH(W)$—$(CH_2)_{n1}$,
—$(CH_2)_{n2}$—$CH(W)$—$(CH_2)_{n3}$;
W represents —$B_1$—$(CF_2)_4F$, $Q_1$-$Z_2$ or $B_1$-$Q_1$-$Z_2$, with $Z_2$ corresponding to $A_1$, $CH(A_1)(A_2)$, $CH_2(A_1)$, $NH(A_1)$, $N(A_1)(A_2)$, $O(A)$ or $S(A_1)$;
for which $A_1$ and $A_2$, identical or different, represent:
—$B_1$—$(CF_2)_4F$, with $B_1$, $B_2$, identical or different, chosen from the groups: $C_1$-$C_{14}$ alkyls;
with $Q_1$ representing $OC(O)$, $C(O)$, $SC(O)$, $NHC(O)$,
$n_1$, $n_2$, $n_3$, identical or different, are between 1 and 4, the sum of $n_2+n_3$ being less than or equal to 4;
taken alone or as a mixture.

As non-limiting examples of monomers capable of being used for the superoleophobic and/or superhydrophobic polymer or copolymer layer 4, 5 or 6, it is possible to cite the following examples:

2-(2H-[1,4]dioxino[2,3-c]pyrrol-6(3H)-yl)ethyl 4,4,5,5,6,6,7,7,7-nonafluoroheptanoate;
2-(2H-[1,4]dithiino[2,3-c]pyrrol-6(3H)-yl)ethyl 4,4,5,5,6,6,7,7,7-nonafluoroheptanoate;
3-(2H-[1,4]dioxino[2,3-c]pyrrol-6(3H)-yl)propyl 4,4,5,5,6,6,7,7,7-nonafluoroheptanoate;
(2H-[1,4]dioxino[2,3-c]pyrrol-6(3H)-yl)dodecyl 4,4,5,5,6,6,7,7,7-nonafluoroheptanoate;
3,3,4,4,5,5,6,6,6-nonafluorohexyl 2-(1H-pyrrol-3-yl)acetate;
thiophen-3-ylmethyl 4,4,5,5,6,6,7,7,7-nonafluoroheptanoate;
2-(thiophen-3-yl)ethyl 4,4,5,5,6,6,7,7,7-nonafluoroheptanoate;
(2,3-dihydrothieno[3,4-b][1,4]dioxin-2-yl)methyl 4,4,5,5,6,6,7,7,7-nonafluoroheptanoate;
S-((2,3-dihydrothieno[3,4-b][1,4]oxathiin-3-yl)methyl) 4,4,5,5,6,6,7,7,7-nonafluoroheptanethioate;
(2,3-dihydrothieno[3,4-b][1,4]oxathiin-2-yl)methyl 4,4,5,5,6,6,7,7,7-nonafluoroheptanoate;
taken alone or as a mixture.

It is also possible to cite the following fluorine-free compounds:
6-decyl-3,6-dihydro-2H-[1,4]dioxino[2,3-c]pyrrole;
6-dodecyl-3,6-dihydro-2H-[1,4]dioxino[2,3-c]pyrrole;
6-tetradecyl-3,6-dihydro-2H-[1,4]dioxino[2,3-c]pyrrole;
2-octyl-2,3-dihydrothieno[3,4-b][1,4]dioxine;
2-decyl-2,3-dihydrothieno[3,4-b][1,4]dioxine;
2-dodecyl-2,3-dihydrothieno[3,4-b][1,4]dioxine;
2-((octyloxy)methyl)-2,3-dihydrothieno[3,4-b][1,4]dioxine;
(2,3-dihydrothieno[3,4-b][1,4]dioxin-2-yl)methyl nonanoate;
2-(thiophen-3-yl) ethyl nonanoate;
2-(2H-[1,4]dioxino[2,3-c]pyrrol-6(3H)-yl)ethyl nonanoate;
(3,4-dihydro-2H-thieno[3,4-b][1,4]dioxepin-3-yl)methyl heptanoate;
(3,4-dihydro-2H-thieno[3,4-b][1,4]dioxepin-3-yl)methyl nonanoate;
(3,4-dihydro-2H-thieno[3,4-b][1,4]dioxepin-3-yl)methyl undecanoate;
(2,3-dihydrothieno[3,4-b][1,4]dioxin-2-yl)methyl isobutyrate;
(2,3-dihydrothieno[3,4-b][1,4]dioxin-2-yl)methyl 2-ethylbutanoate;
(2,3-dihydrothieno[3,4-b][1,4]dioxin-2-yl)methyl 2-propylpentanoate;
taken alone or as a mixture.

It is also possible to cite the following short-chain fluorinated compounds:
12-(2H-[1,4]dioxino[2,3-c]pyrrol-6(3H)-yl)-N-(3,3,4,4,5,5,6,6,6-nonafluorohexyl)dodecanamide;
S-((2,3-dihydrothieno[3,4-b][1,4]oxathiin-2-yl)methyl) 4,4,5,5,6,6,7,7,7-nonafluoroheptanethioate;
(3,4-dihydro-2H-thieno[3,4-b][1,4]dioxepin-3-yl)methyl 4,4,5,5,6,6,7,7,7-nonafluoroheptanoate;
6-(2H-[1,4]dioxino[2,3-c]pyrrol-6(3H)-yl)hexyl 4,4,5,5,6,6,7,7,7-nonafluoroheptanoate;
1-((2,3-dihydrothieno[3,4-b][1,4]dioxin-2-yl)methyl)-3-(2,2,3,3,4,4,5,5,5-nonafluoropentyl)urea;
2,2,3,3,4,4,5,5,5-nonafluoropentyl ((2,3-dihydrothieno[3,4-b][1,4]dioxin-2-yl)methyl)carbamate;
(2,3-dihydrothieno[3,4-b][1,4]dioxin-2-yl)methyl (2,2,3,3,4,4,5,5,5-nonafluoropentyl)carbamate;
12-((2,3-dihydrothieno[3,4-b][1,4]dioxin-2-yl)methoxy)-N-(2,2,3,3,4,4,5,5,6,6-undecafluorohexyl)dodecanamide;
taken alone or as a mixture.

Surprisingly, the applicant was able to demonstrate that the material according to the invention, comprised of the constituents described above, is actually superoleophobic and/or superhydrophobic, while simultaneously having anti-adhesion, anti-friction and/or anti-corrosion properties, but also improved stability, in particular in terms of adhesion and cohesion with the substrate. That is to say that the polymer or copolymer layers adhere better to the substrate with a surface that is modified and/or that integrates a first adhesion-promoting conductive layer as described above.

Specifically, as described in the examples and illustrated in FIGS. 4 to 9, the applicant demonstrated that the material according to the invention was particularly stable over time when the superposition of the different constituents have an increasing hydrophobicity gradient between the first layer deposited on the conductive substrate or substrate previously rendered conductive 1 and the last layer of said material. Nothing in the prior art documents that teaches or describes that it would be useful and advantageous to have a superposition of polymer or copolymer layers as described above, with an increasing hydrophobicity gradient, in order to obtain superoleophobic and/or superhydrophobic materials having improved properties, in particular adhesion properties.

The applicant was able to demonstrate that it is very difficult or even impossible to deposit the superhydrophobic or superoleophobic layer according to the invention directly on the support, without a preliminary surface treatment or addition of a promoter.

Figure 1:
FIG. 1 shows, in the upper portion, the absence of adhesion of a superhydrophobic coating without an adhesion promoter. In the lower portion of FIG. 1, it is possible to observe that the superhydrophobic coating is on Scotch tape and not on the substrate.

The applicant was able to observe numerous different phenomena on the basis of the type of monomer used. For example, it was impossible to deposit EDOTF6-type monomers on a steel substrate. The deposition of an EDOTF4 monomer made it possible to obtain a copolymer surface having a very low adhesion (cf. FIG. 1, adhesion result 0B according to the ASTM D 3359 method). In addition, the deposition was not homogeneous and it was impossible to find intrinsic properties of superoleophobic and/or superhydrophobic materials.

Advantageously, the material according to the invention also includes one or more additional polymer or copolymer layers 5, 6, which are superimposed on the first polymer or copolymer layer 4 described above, according to an increasing hydrophobicity gradient.

Figure 9:
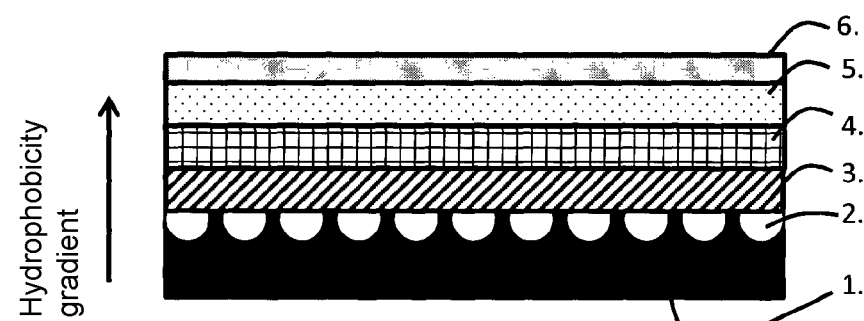

In other words, as shown in FIG. 9, the polymer or copolymer layer 6 located on the outer surface of the material has a hydrophobicity greater than the lower layers 3, 4 and 5, optionally modified by a chemical or physical treatment 2.

A second object of the invention relates to a process for producing a superoleophobic and/or superhydrophobic material according to the invention including the steps of:
physical and/or chemical treatment 2 of a conductive substrate or substrate previously rendered conductive 1 and/or deposition of an adhesion-promoting conductive layer 3 on said substrate;
deposition on the adhesion-promoting conductive layer 3 of at least one superoleophobic and/or superhydrophobic polymer or copolymer layer 4, 5 or 6 comprised of one or more monomers based on an aromatic or heteroaromatic ring substituted by one or more fluorocarbon and/or hydrocarbon chains; and
recovery of the superoleophobic and/or superhydrophobic material.

Preferably the substrate is deposited in a conductive bath comprised of an ionic or organic liquid or an emulsion or a microemulsion, and anhydric acetonitrile or a water-based mixture containing a salt or an electrolytes such as, in particular tetrabutylammonium hexafluorophosphoate (Bu4NPF6).

The physical and/or chemical treatments, the polymer or copolymer layer are as described above.

A third object of the invention concerns a fluorine-free monomer, responding to the general formula (I):

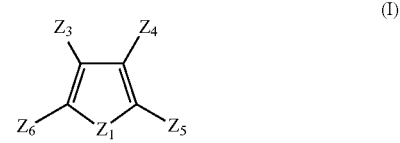

(I)

wherein:
$Z_1$ is chosen from the atoms and groups S, O, NH and N—W;
$Z_3$ is chosen from the atoms and groups H, $X_1$—W, $X_1$—$R_1$—$X_2$, $C(R_2)(R_3)$;
$Z_4$ is chosen from the atoms and groups W, $X_1$—W, $X_1$—$R_1$—$X_2$, $C(R_2)(R_3)$;
$Z_5$ and $Z_6$ represent an H atom or a hydrocarbon chain including 3 carbon atoms;
wherein:
W represents $B_1$—H, $Q_1$-$Z_2$ or $B_1$-$Q_1$-$Z_2$;
 with $B_1$, $B_2$, $B_3$, identical or different, chosen from the groups: $C_1$-$C_{20}$ alkyls, $C_1$-$C_{20}$ alkenyls, $C_1$-$C_{20}$ alkynyls, $C_6$-$C_{18}$ aryls, $C_6$-$C_{18}$ heteroaryls;
 with $Z_2$ corresponding to $A_1$, $CH(A_1)(A_2)$, $CH_2(A_1)$, $NH(A_1)$, $N(A_1)(A_2)$, $O(A_1)$ or $S(A_1)$;
for which $A_1$ and $A_2$, identical or different, represent:
—$B_2$—H,
—$B_3$-ph-$Q_2$-$B_2$—H; "ph" designating the functional phenyl group;
 with $Q_1$ and $Q_2$, identical or different, which represent OC(O), C(O), SC(O), NHC(O);
$X_1$ and $X_2$, identical or different, are chosen from the atoms or groups O, S, NH;
$R_1$ is chosen from the groups —CH(W)—, —$(CH_2)_{n1}$—CH(W)—, —CH(W)—$(CH_2)_{n1}$, —$(CH_2)_{n2}$—CH(W)—$(CH_2)_{n3}$—; and
—$(CH_2)_{n1}$— when $Z_1$ equals N—W; W being as defined above and $n_1$, $n_2$, $n_3$, identical or different, are between 1 and 12, the sum of $n_2$+$n_3$ being less than or equal to 12;
$R_2$ is a hydrocarbon chain including 3 carbon atoms;
$R_3$ is chosen from the groups W, $X_1$—W or $X_1$—$R_1$—$X_2$;
and wherein:
when $Z_3$ and $Z_4$ correspond to $X_1$—$R_1$—$X_2$, they are linked to one another to form a ring;
when $Z_3$ and/or $Z_4$ correspond to $C(R_2)(R_3)$, they are linked to $Z_6$ and $Z_5$, ($Z_6$ and $Z_3$) and ($Z_5$ and $Z_4$), to form a 6-carbon aromatic ring, and when $R_3$ corresponds to $X_1$—$R_1$—$X_2$, then $Z_3$ and $Z_4$ are linked to one another and also form a ring;
and wherein, when $Z_1$ is an S atom:
if $Z_3$ is an H atom, then $Z_4$ is chosen from the groups $X_1$—W or $C(R_2)(R_3)$;
$Z_3$ and $Z_4$ cannot simultaneously be equal to OW;
and wherein, when $Z_1$ is an S or NW atom:
if $Z_3$ and $Z_4$ correspond to $X_1$—$R_1$—$X_2$, $n_1$ is equal to 1 and $Z_2$ corresponds to $CH_2(A_1)$ then $B_2$, $B_3$, identical or different, are chosen from the groups: $C_1$-$C_{20}$ alkenyls, $C_1$-$C_{20}$ alkynyls, $C_6$-$C_{18}$ aryls, $C_6$-$C_{18}$ heteroaryls;

and wherein, when $Z_1$ is N—W and W corresponds to $B_1$—H, then $B_1$ is chosen from the groups: $C_1$-$C_{20}$ alkenyls, $C_1$-$C_{20}$ alkynyls, $C_6$-$C_{18}$ aryls, $C_6$-$C_{18}$ heteroaryls.

Preferably, the fluorine-free monomer responding to the usable general formula (I) is such that:
$Z_1$ is chosen from the atoms and groups S, NH and N—W;
$Z_3$ is chosen from the atoms and groups H, $X_1$—W, $X_1$—$R_1$—$X_2$;
$Z_4$ is chosen from the atoms and groups W, $X_1$—W, $X_1$—$R_1$—$X_2$;
$Z_5$ and $Z_6$ represent an H atom;
wherein:
W represents $B_1$—H, $Q_1$-$Z_2$ or $B_1$-$Q_1$-$Z_2$;
  with $B_1$, $B_2$, $B_3$, identical or different, chosen from the groups: $C_1$-$C_{16}$ alkyls, $C_1$-$C_{16}$ alkenyls, $C_1$-$C_{16}$ alkynyls, $C_6$-$C_{18}$ aryls, $C_6$-$C_{18}$ heteroaryls;
  with $Z_2$ corresponding to $A_1$, $CH(A_1)(A_2)$, $CH_2(A_1)$, $NH(A_1)$, $N(A_1)(A_2)$, $O(A_1)$ or $S(A_1)$;
  for which $A_1$ and $A_2$, identical or different, represent:
  —$B_2$—H,
  —$B_3$-ph-$Q_2$-$B_2$—H; "ph" designating the functional phenyl group;
  with $Q_1$ and $Q_2$, identical or different, which represent OC(O), C(O), SC(O), NHC(O);
$X_1$ and $X_2$, identical or different, are chosen from the atoms or groups O, S;
$R_1$ is chosen from the groups —CH(W)—, —$(CH_2)_{n1}$—CH(W)—, —CH(W)—$(CH_2)_{n1}$, —$(CH_2)_{n2}$—CH(W)—$(CH_2)_{n3}$— and
—$(CH_2)_{n1}$, when $Z_1$ equals N—W; W being as defined above and $n_1$, $n_2$, $n_3$, identical or different, are between 1 and 4, the sum of $n_2$+$n_3$ being less than or equal to 4;
and wherein:
when $Z_3$ and $Z_4$ correspond to $X_1$—$R_1$—$X_2$, they are linked to one another to form a ring;
and wherein, when $Z_1$ is an S atom:
if $Z_3$ is an H atom, then $Z_4$ is chosen from the groups $X_1$—W or $C(R_2)(R_3)$;
$Z_3$ and $Z_4$ cannot simultaneously be equal to OW;
and wherein, when $Z_1$ is an S or NW atom:
if $Z_3$ and $Z_4$ correspond to $X_1$—$R_1$—$X_2$, $n_1$ is equal to 1 and W represents $B_1$-$Q_1$-$Z_2$ with $Z_2$ corresponding to $CH_2(A_1)$, then $B_2$, $B_3$, identical or different, are chosen from the groups: $C_1$-$C_{16}$ alkenyls, $C_1$-$C_{16}$ alkynyls, $C_6$-$C_{18}$ aryls, $C_6$-$C_{18}$ heteroaryls;
and wherein, when $Z_1$ is N—W and W corresponds to $B_1$—H, then $B_1$ is chosen from the groups: $C_1$-$C_{16}$ alkenyls, $C_1$-$C_{16}$ alkynyls, $C_6$-$C_{18}$ aryls, $C_6$-$C_{18}$ heteroaryls.

Particularly advantageously, the fluorine-free monomer is chosen from the following compounds of formula (II):

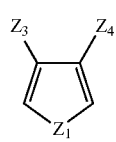

(II)

wherein:
$Z_1$ is chosen from the atoms and groups S, NH and NW;
$Z_3$ and $Z_4$ represent $X_1$—$R_1$—$X_2$ and are linked to one another to form a ring:
$X_1$ and $X_2$ are chosen from the atoms and groups O, S;
$R_1$ is chosen from the following groups:
—CH(W), —$(CH_2)_{n1}$—CH(W)—,
—CH(W)—$(CH_2)_{n1}$,
—$(CH_2)_{n2}$—CH(W)—$(CH_2)_{n3}$;
W represents —$B_1$—H, $Q_1$-$Z_2$ or $B_1$-$Q_1$-$Z_2$, with $Z_2$ corresponding to $A_1$, $CH(A_1)(A_2)$, $CH_2(A_1)$, $NH(A_1)$, $N(A_1)(A_2)$, $O(A_1)$ or $S(A_1)$;
for which $A_1$ and $A_2$, identical or different, represent:
—$B_2$—H, with $B_1$, $B_2$, identical or different, chosen from the groups: $C_1$-$C_{16}$ alkyls, $C_1$-$C_{16}$ alkenyls, $C_1$-$C_{16}$ alkynyls, $C_6$-$C_{18}$ aryls, $C_6$-$C_{18}$ heteroaryls;
with $Q_1$ representing OC(O), C(O), SC(O), NHC(O),
$n_1$, $n_2$, $n_3$, identical or different, are between 1 and 4, the sum of $n_2$+$n_3$ being less than or equal to 4;
and wherein, when $Z_1$ is an S atom or an N—W group: if $n_1$ is equal to 1 and $Z_2$ corresponds to $CH_2(A_1)$ then $B_2$, $B_3$, identical or different, are chosen from the groups: $C_1$-$C_{16}$ alkenyls, $C_1$-$C_{16}$ alkynyls, $C_6$-$C_{18}$ aryls, $C_6$-$C_{18}$ heteroaryls;
and wherein, when $Z_1$ is N—W and W corresponds to $B_1$—H, then $B_1$ is chosen from the groups: $C_1$-$C_{16}$ alkenyls, $C_1$-$C_{16}$ alkynyls, $C_6$-$C_{18}$ aryls, $C_6$-$C_{18}$ heteroaryls.

A fourth object of the invention concerns a short-chain fluorinated monomer of formula (I) wherein:
$Z_1$ is chosen from the atoms and groups S, O, NH and N—W;
$Z_3$ is chosen from the atoms and groups H, $X_1$—W, $X_1$—$R_1$—$X_2$, $C(R_2)(R_3)$;
$Z_4$ is chosen from the atoms and groups W, $X_1$—W, $X_1$—$R_1$—$X_2$, $C(R_2)(R_3)$;
$Z_5$ and $Z_6$ represent an H atom or a hydrocarbon chain including 3 carbon atoms;
wherein:
W represents $(CF_2)_qF$, $B_1$—$(CF_2)_pF$, $Q_1$-$Z_2$ or $B_1$-$Q_1$-$Z_2$;
  with $B_1$, $B_2$, $B_3$, identical or different, chosen from the groups: $C_1$-$C_{20}$ alkyls, $C_1$-$C_{20}$ alkenyls, $C_1$-$C_{20}$ alkynyls, $C_6$-$C_{18}$ aryls, $C_6$-$C_{18}$ heteroaryls;
  with $Z_2$ corresponding to $A_1$, $CH(A_1)(A_2)$, $CH_2(A_1)$, $NH(A_1)$, $N(A_1)(A_2)$, $O(A_1)$ or $S(A_1)$;
for which $A_1$ and $A_2$, identical or different, represent:
—$B_2$—$(CF_2)_pF$,
—$B_3$-ph-$Q_2$-$B_2$—$(CF_2)_pF$; "ph" designating the functional phenyl group;
with q and p being between 1 and 6;
with $Q_1$ and $Q_2$, identical or different, which represent OC(O), C(O), SC(O), NHC(O);
$X_1$ and $X_2$, identical or different, are chosen from the atoms or groups O, S, NH;
$R_1$ is chosen from the groups —CH(W)—, —$(CH_2)_{n1}$—CH(W)—, —CH(W)—$(CH_2)_{n1}$, —$(CH_2)_{n2}$—CH(W)—$(CH_2)_{n3}$— and
—$(CH_2)_{n1}$, when $Z_1$ equals N—W; W being as defined above and $n_1$, $n_2$, $n_3$, identical or different, are between 1 and 12, the sum of $n_2$+$n_3$ being less than or equal to 12;
$R_2$ is a hydrocarbon chain including 3 carbon atoms;
$R_3$ is chosen from the groups W, $X_1$—W or $X_1$—$R_1$—$X_2$;
and wherein:
when $Z_3$ and $Z_4$ correspond to $X_1$—$R_1$—$X_2$, they are linked to one another to form a ring;
when $Z_3$ and/or $Z_4$ correspond to $C(R_2)(R_3)$, they are linked to $Z_6$ and $Z_5$, ($Z_6$ and $Z_3$) and ($Z_5$ and $Z_4$), in order to form a 6-carbon aromatic ring, and when $R_3$ corresponds to $X_1$—$R_1$—$X_2$ then $Z_3$ and $Z_4$ are linked to one another and also form a ring;
and wherein, when $Z_1$ is an S atom or an NH group:
if $Z_3$ is an H atom, then $Z_4$ is chosen from the groups $X_1$—W or $C(R_2)(R_3)$;

and wherein, when $Z_1$ is an S atom or the N—W group:
if $Z_3$ and $Z_4$ correspond to $X_1$—$R_1$—$X_2$, $n_1$ is equal to 1 while $Q_1$ is chosen from C(O) and NHC(O) so that $Z_2$ corresponds to $A_1$, CH($A_1$)($A_2$), CH$_2$($A_1$), NH($A_1$), N($A_1$)($A_2$) or S($A_1$).

Preferably, the short-chain fluorinated monomer responding to the usable general formula (I) is such that:
$Z_1$ is chosen from the atoms and groups S, NH and N—W;
$Z_3$ is chosen from the atoms and groups H, $X_1$—W, $X_1$—$R_1$—$X_2$;
$Z_4$ is chosen from the atoms and groups W, $X_1$—W, $X_1$—$R_1$—$X_2$;
$Z_5$ and $Z_6$ represent an H atom;
wherein:
W represents $(CF_2)_4F$, $B_1$—$(CF_2)_4F$, $Q_1$-$Z_2$ or $B_1$-$Q_1$-$Z_2$;
with $B_1$, $B_2$, $B_3$, identical or different, chosen from the groups: $C_1$-$C_{14}$ alkyls;
with $Z_2$ corresponding to $A_1$, CH($A_1$)($A_2$), NH($A_1$), N($A_1$)($A_2$), O($A_1$) or S($A_1$);
for which $A_1$ and $A_2$, identical or different, represent:
—$B_2$—$(CF_2)_4F$,
—$B_3$-ph-$Q_2$-$B_2$—$(CF_2)_4F$; "ph" designating the functional phenyl group;
with $Q_1$ and $Q_2$, identical or different, which represent OC(O), C(O), SC(O), NHC(O);
$X_1$ and $X_2$, identical or different, are chosen from the atoms or groups O, S;
$R_1$ is chosen from the groups —CH(W)—, —$(CH_2)_{n1}$—CH(W)—, —CH(W)—$(CH_2)_{n1}$, —$(CH_2)_{n2}$—CH(W)—$(CH_2)_{n3}$— and
—$(CH_2)_{n1}$, when $Z_1$ equals N—W; W being as defined above and $n_1$, $n_2$, $n_3$, identical or different, are between 1 and 4, the sum of $n_2+n_3$ being less than or equal to 4;
and wherein:
when $Z_3$ and $Z_4$ correspond to $X_1$—$R_1$—$X_2$, they are linked to one another to form a ring;
and wherein, when $Z_1$ is an S atom or an NH group:
if $Z_3$ is an H atom, then $Z_4$ is chosen from the groups $X_1$—W;
and wherein, when $Z_1$ is an S atom or the N—W group:
if $Z_3$ and $Z_4$ correspond to $X_1$—$R_1$—$X_2$ and $n_1$ is equal to 1 while $Q_1$ is chosen from C(O) and NHC(O) so that $Z_2$ corresponds to $A_1$, CH($A_1$)($A_2$), CH$_2$($A_1$), NH($A_1$), N($A_1$)($A_2$) or S($A_1$).

Particularly advantageously, the short-chain fluorinated monomer is chosen from the compounds of formula (II):

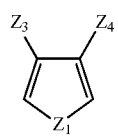

(II)

wherein:
$Z_1$ is chosen from the atoms and groups S, NH and N—W;
$Z_3$ and $Z_4$ represent $X_1$—$R_1$—$X_2$ and are linked to one another to form a ring:
$X_1$ and $X_2$ are chosen from the atoms and groups O and S;
$R_1$ is chosen from the following groups:
—CH(W)—, —$(CH_2)_{n1}$—CH(W)—
—CH(W)—$(CH_2)_{n1}$,
—$(CH_2)_{n2}$—CH(W)—$(CH_2)_{n3}$—

W represents —$B_1$—$(CF_2)_4F$, $Q_1$-$Z_2$ or $B_1$-$Q_1$-$Z_2$, with $Z_2$ corresponding to $A_1$, CH($A_1$)($A_2$), CH$_2$($A_1$), NH($A_1$), N($A_1$)($A_2$), O($A_1$) or S($A_1$);
for which $A_1$ and $A_2$, identical or different, represent:
—$B_1$—$(CF_2)_4F$, with $B_1$, $B_2$, identical or different, chosen from the groups: $C_1$-$C_{14}$ alkyls;
with $Q_1$ representing OC(O), C(O), SC(O), NHC(O),
$n_1$, $n_2$, $n_3$, identical or different, are between 1 and 4, the sum of $n_2+n_3$ being less than or equal to 4;
and wherein, when $Z_1$ is an S atom or the N—W group:
if $Z_3$ and $Z_4$ correspond to $X_1$—$R_1$—$X_2$, $n_1$ is equal to 1 while $Q_1$ is chosen from C(O) and NHC(O) so that $Z_2$ corresponds to $A_1$, CH($A_1$)($A_2$), CH$_2$($A_1$), NH($A_1$), N($A_1$)($A_2$) or S($A_1$).

A fifth object of the invention concerns a superoleophobic and/or superhydrophobic polymer or copolymer layer comprised of one or more fluorine-free or short-chain fluorinated monomers, of formula (I) or (II), wherein the groups are as defined above.

A sixth object of the invention concerns a superoleophobic and/or superhydrophobic material including, on the one hand, a first constituent that is a conductive substrate or a substrate previously rendered conductive 1:
the surface of which it modified by a chemical and/or physical treatment;
and/or
integrating at least one first adhesion-promoting conductive layer;
and, on the other hand, at least one superoleophobic and/or superhydrophobic polymer or copolymer layer comprised of one or more fluorine-free or short-chain fluorinated monomers, of formula (I) or (II), wherein the groups are as defined above.

Finally, a seventh object of the invention concerns the use of a material according to the invention as an anti-adhesion, anti-friction and/or anti-corrosion material.

Among the anti-adhesion applications capable of being envisaged according to the invention, the materials according to the invention may, for example, make it possible to:
prevent bacterial contamination of medical surfaces or the like;
reduce the absorption of graffiti, i.e. inscriptions, slogans or painted drawings, sprayed or etched on a wall or on a surface, which are not normally intended for this purpose;
reduce finger marks, in particular on electrical household appliances or mobile telephones or computers;
facilitate the cleaning of pans;
reduce the footprint on new planets by reducing contaminations;
reduce stains on clothing;
reduce airplane cleaning costs;
improve the reception of information in instruments enabling the pressure to which an airplane is subjected to be measured in order to deduce the speed thereof (pitot probes);
increase the specific impermeability of clothing to liquids;
improve insulation, in particular of roofs;
prevent biological contamination, in particular in the case of biological targets; this may generate anti-bioadhesion or, conversely, bioadhesion or a specificity of bioadhesion or anti-bioadhesion according to surface morphology;
protect urban paint from pollution;
reduce the maintenance of optical systems, in particular telescope lenses, eyeglasses, microscopes;
avoid cleaning windows;

reduce the costs of maintenance and the loss of luminosity on photovoltaic panels;
improve visibility on windshields.

Among the anti-friction applications capable of being envisaged according to the invention, the materials according to the invention may, for example, make it possible to:
reduce the consumption of boats;
improve the maneuverability of boats;
improve the gliding behavior in gliding sports and games, such as, in particular, skiing, snowboarding and luge;
improve the performance of swimmers and divers;
reduce fuel consumption such as kerosene;
increase the flow of a fluid over a surface;
reduce frost on blades, in particular helicopter blades;
improve the efficiency of turbines;
reduce the formation of frost on airplanes;
reduce the formation of frost on cables or heat exchangers; and
improve the efficiency of engines.

Among the anti-corrosion applications capable of being envisaged according to the invention, the materials according to the invention may, for example, make it possible to:
improve protection against corrosion of boat hulls and all submerged materials such as probes, buoys, drive shafts and propellers;
increase the water resistance of electronic components; and
improve the lifetime of electronic components.

Of course, the invention is not limited to the embodiments described and shown in the appended figures, and a person skilled in the art will be led, by routine operations, to produce other embodiments not explicitly described, without going beyond the context and scope of the present invention.

EXAMPLE 1: EXAMPLE EMBODIMENT OF A SUPERHYDROPHOBIC MULTILAYER COATING

For this example, the applicant developed superhydrophobic coatings including two layers:
polypyrrole as an adhesion promoter, and
a superhydrophobic fluorinated polymer, which is PEdot-F4.

PEdot-F4 is a polymer including Edot-F4 monomers responding to the following general formula:

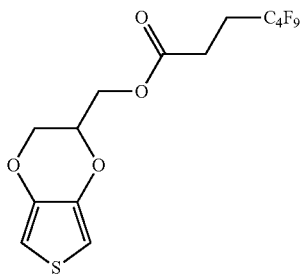

The two polymers above are deposited by chronoamperometry electrodeposition (with potential step). The oxidation potential is determined first by cyclic voltammetry at 0.1 V/s, from 0 V to 2 V.

In the electrochemical cell, the counter-electrode is a platinum plate and the reference electrode is a saturated calomel electrode. The electrolyte solution is degassed before the experiment.

The polypyrrole deposition was performed in different solvents (acetonitrile and water). Multiple electrodes may be used:
lithium perchlorate, and
sulfuric acid in acetonitrile,
fluorosulfonic acid, and
oxalic acid (dihydrate) in water.

The polypyrrole film is around 20 nanometers or tens of nanometers in thickness.

The polypyrrole is deposited in ultrapure water (R>18.2 MΩ·cm) using oxalic acid dihydrate (57 mM) as an electrolyte. The working electrode used is a 316 stainless steel plate.

The polypyrrole charge deposited is 5 mC/cm$^2$ with an oxidation potential of 0.75 V±0.03 V vs. SCE.

After deposition, the surface is washed with ultrapure water and dried.

The Edot-F4 monomer, the general formula of which is provided above, is electrodeposited on the polypyrrole film. The polymerization is performed in the electrolyte comprised of anhydrous acetonitrile and lithium perchlorate or tetrabutylammonium hexafluorophosphate. The working electrode is 316 stainless steel coated with 5 mC/cm$^2$ of polypyrrole. The deposited charge of PEdot-F4 is 10 mC/cm$^2$ with an oxidation potential of 1.43 V±0.05 V vs. SCE.

After deposition, the surface is washed with acetonitrile and dried.

The water contact angle of the coating as prepared is around 160°.

An adhesion test was then performed, according to the ASTM D 3359 method.

Figure 2:
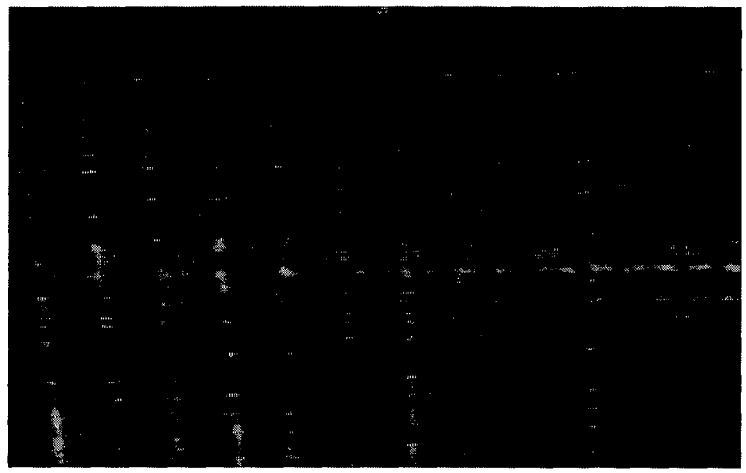
FIG. 2 shows a photographic image of the adhesion of an adhesion promoter which is polypyrrole.
Figure 3:
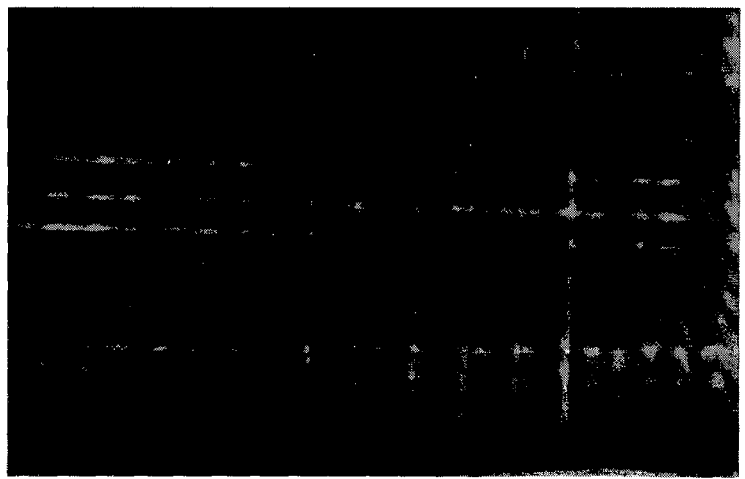
FIG. 3 shows a photographic image of the adhesion of a superhydrophobic coating with an adhesion promoter that is polypyrrole on stainless steel 316.
Figure 4:
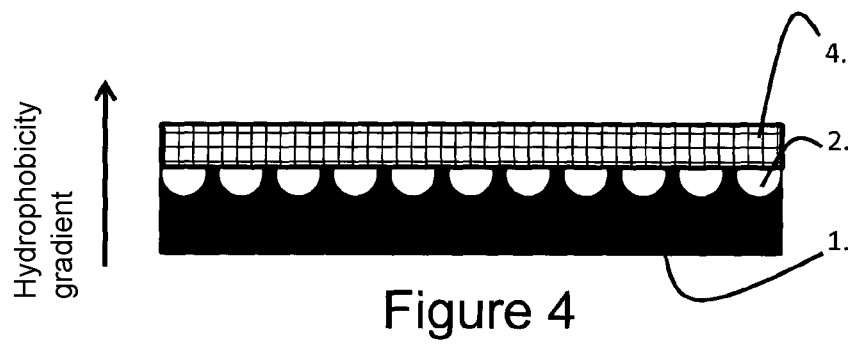
Figure 5:
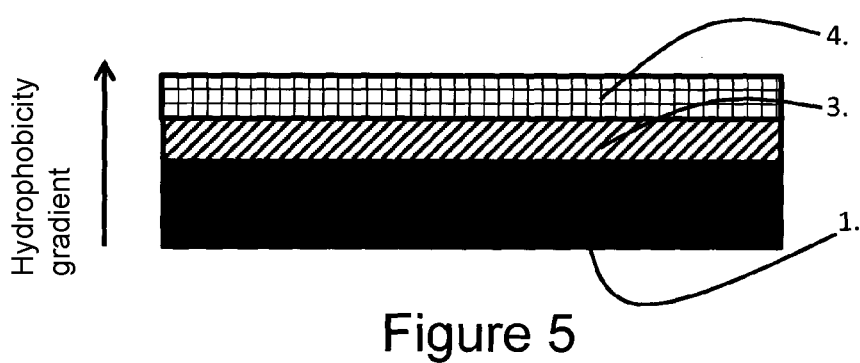
Figure 6:
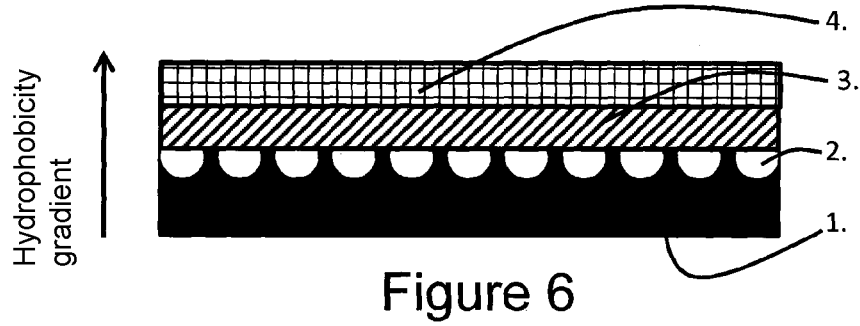
Figure 7:
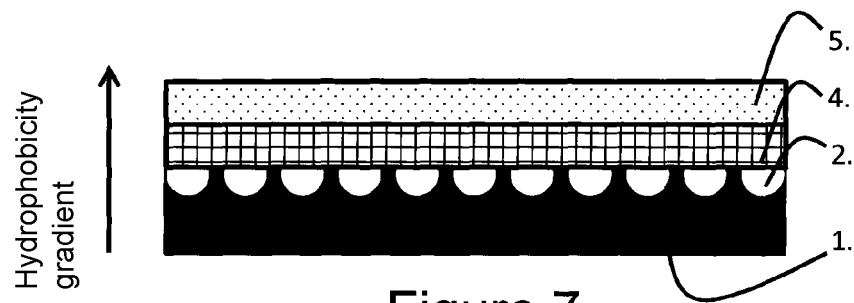
Figure 8:
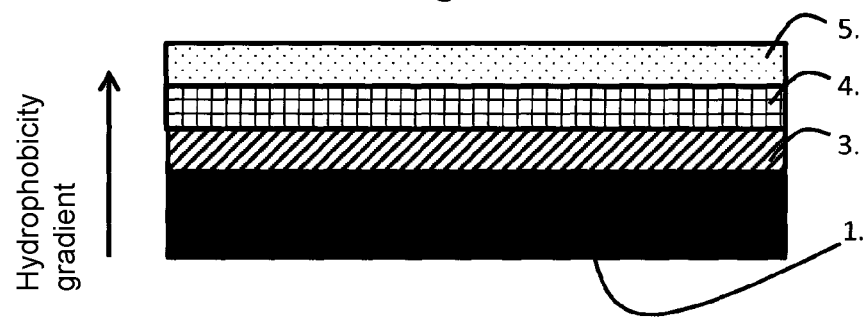

The result of this test is reproduced in FIGS. 2 and 3. It shows that the adhesions of the polypyrrole coating and the superhydrophobic coating with polypyrrole on 316 stainless steel are excellent. The edges of the cuts are entirely smooth and none of the grid squares is detached.

EXAMPLE 2: PREPARATION OF SUPERHYDROPHOBIC MATERIAL ACCORDING TO THE INVENTION AND ASSOCIATED SUPERHYDROPHOBICITY AND ADHESION TESTS

For this example, sixteen different materials were produced, for which the water contact angle was calculated. An adhesion test was also performed for each material, according to the ASTM D 3359 method.

Before any treatment, metal surfaces, which constitute the conductive substrate of the material, were cleaned with ultrasound for 15 minutes in ethanol, then were rinsed in ethanol and dried. The metal surfaces used are steel, but deposits on platinum give substantially identical results (data not described below). Other surfaces such as aluminum also enable the deposition of pyrrol.

Then, on the substrate, oxygen plasma or argon plasma treatments, a self-assembled monolayer SAM grafting and/or one or two electrodepositions were performed.

The detail of the different procedures of these steps is described below:
a. Plasma O2:

After cleaning, the steel surfaces are treated with oxygen plasma under a flow of 10 sccm at 300 W for 1 minute. The electrodeposition of the superhydrophobic polymer is performed immediately after this treatment.

b. Plasma Ar:

After cleaning, the steel surfaces are treated with argon plasma under a flow of 10 sccm at 300 W for 1 minute. The electrodeposition of the superhydrophobic polymer is performed immediately after this treatment.

c. *Aqua Regia:*

After cleaning, the substrate is submerged for 10 minutes in an *aqua regia* solution (hydrochloric acid/nitric acid in proportions of 3:1), then it is rinsed with demineralized water and dried.

d. Self-Assembled Monolayer (SAM):

The grafted molecules are acids such as, for example, undecylenic acid, decanoic acid, linoleic acid or octadecyl phosphonic acid or 11-(1H-pyrrol-1-yl)undecane-1-thiol.

After cleaning the steel surfaces are submerged in a 2.5 mM solution in absolute ethanol for 12 h. The surfaces are then rinsed with absolute ethanol, then dried.

e. Electrodeposition of Acetonitrile/LiClO4 Pyrrole:

The electrochemical polymerization of the pyrrole is performed in a solution containing 0.01 M of monomer with lithium perchlorate (0.1 M) as an electrolyte.

The polypyrrole is a conductive polymeric layer, the thickness of which must preferably be below 0.1 micrometers. The ideal thickness being between 1 and 50 nanometers. Still more preferably, the ideal thickness is around 20 nm.

The solvent used is anhydrous acetonitrile.

The deposited surface charge is around 5 mC/cm$^2$ with a working potential of 1.5 V to 1.9 V according to the presence of a preliminary treatment.

The counter-electrode is a platinum plate and the reference electrode is a saturated calomel electrode (SCE).

After deposition, the surface is rinsed in the solvent.

f. Electrodeposition of Water/H2SO4 Pyrrole:

The electrochemical polymerization of the pyrrole is performed in a solution containing 0.01 M of monomer with sulfuric acid (0.1 M) as an electrolyte. The solvent used is ultrapure water.

The deposited surface charge is 5 mC/cm$^2$ with a working potential of around 1 V.

The counter-electrode is a platinum plate and the reference electrode is a saturated calomel electrode (SCE).

After deposition, the surface is rinsed in the solvent.

g. Electrodeposition of Water/Paratoluene-Sulfonic Acid Pyrrole:

The electrochemical polymerization of the pyrrole is performed in a solution containing 0.25 M of monomer with paratoluenesulfonic acid (1 M) as an electrolyte. The solvent used is ultrapure water.

The deposited surface charge is 20 mC/cm$^2$ with a working potential of around 0.70 V.

The counter-electrode is a platinum plate and the reference electrode is a saturated calomel electrode (SCE).

After deposition, the surface is rinsed in the solvent.

h. Electrodeposition of Pyrrole/Aniline Water/Oxalic Acid Copolymer:

The electrochemical polymerization of the pyrrole/aniline copolymer is performed in a solution containing 0.1 M of each monomer with oxalic acid dihydrate (0.25 M) as an electrolyte. The solvent used is ultrapure water.

The deposited surface charge is 7 mC/cm$^2$ with a working potential of around 1.05 V.

The counter-electrode is a platinum plate and the reference electrode is a saturated calomel electrode (SCE).

After deposition, the surface is rinsed in the solvent.

i. Electrodeposition of Acetonitrile/HFSO3 Pyrrole:

The electrochemical polymerization of the pyrrole is performed in a solution containing 0.01 M of monomer with fluorosulfonic acid (0.01 M) as an electrolyte. The solvent used is anhydrous acetonitrile.

The deposited surface charge is 5 mC/cm$^2$ with a working potential of around 1.6 V.

The counter-electrode is a platinum plate and the reference electrode is a saturated calomel electrode (SCE).

After deposition, the surface is rinsed in the solvent.

j. Electrodeposition of Water/Oxalic Acid Pyrrole:

The electrochemical polymerization of the pyrrole is performed in a solution containing 0.25 M of monomer with oxalic acid dihydrate (0.057 M) as an electrolyte. The solvent used is anhydrous acetonitrile.

The deposited surface charge is 5 mC/cm$^2$ with a working potential of around 0.75 V.

The counter-electrode is a platinum plate and the reference electrode is a saturated calomel electrode (SCE).

After deposition, the surface is rinsed in the solvent.

k. Electrodeposition of Superhydrophobic Acetonitrile/LiClO4 Polymer:

The electrochemical polymerization of the superhydrophobic polymers is performed in a solution containing 0.01 M of monomer with lithium perchlorate (0.1 M) as an electrolyte.

The superhydrophobic polymers used are as follows:

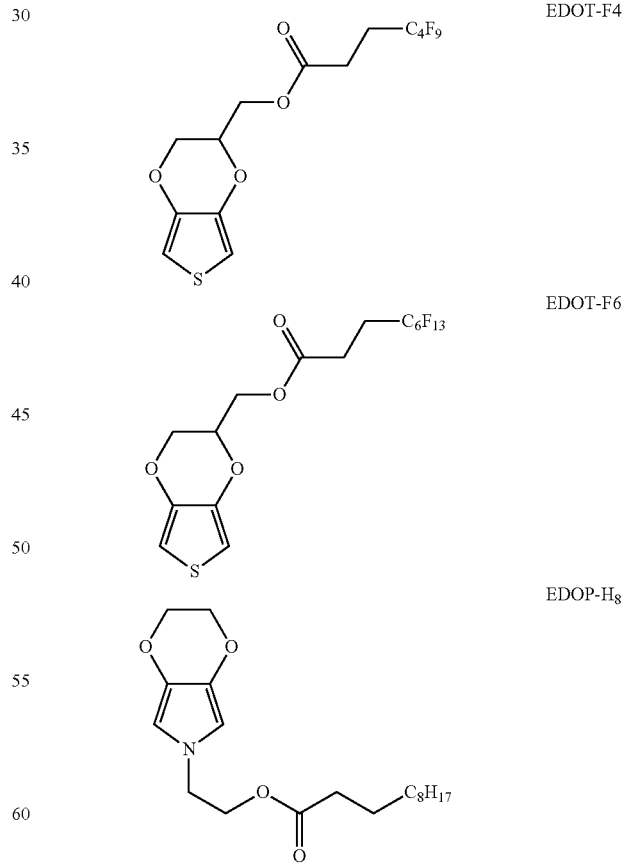

The solvent used is anhydrous acetonitrile.

The deposited surface charge is 5 mC/cm$^2$ with a working potential of around 1.5 V to 1.9 V according to the presence of a preliminary treatment.

The counter-electrode is a platinum plate and the reference electrode is a saturated calomel electrode (SCE).

After deposition, the surface is rinsed in the solvent.

The detail of the different constituents of the sixteen materials produced is presented in table 1 below. Table 1 also shows the results of the measurements of the water contact angle (WCA) as well as the results of the adhesion test according to the ASTM D 3359 method. It should be noted that the results showing low adhesions (result 0B) presented in table 1 correspond to copolymer layers having a homogeneous deposition and enabling the intrinsic properties of the superoleophobic and/or superhydrophobic materials to be found. This is therefore an improvement with respect to the results obtained for depositions without a surface treatment or the use of a promoter observed above in FIG. 1.

TABLE 1

| Substrate | Plasma or chemical etching | SAM | Electro-deposition 1 | Electro-deposition 2 (SH polymer) | WCA | Adhesion tests according to ASTM D 3359 standard |
|---|---|---|---|---|---|---|
| Steel | | Undecylenic acid | | Edot-F6 100 mC Acetonitrile/LiClO4 | 153° | 0B |
| Steel | | Octadecyl phosphonic acid | | Edot-F6 100 mC Acetonitrile/LiClO4 | 153° | 0B |
| Steel | | | 10 mC Pyrrole Acetonitrile/LiClO4 | Edot-F6 100 mC Acetonitrile/LiClO4 | 151° | 0B |
| Steel | Plasma O2 | | 10 mC Pyrrole Acetonitrile/LiClO4 | Edot-F6 100 mC Acetonitrile/LiClO4 | 150° | 0B |
| Steel | Plasma Ar | | 10 mC Pyrrole Acetonitrile/LiClO4 | Edot-F6 100 mC Acetonitrile/LiClO4 | 151° | 0B |
| Steel | | Octadecyl phosphonic acid | 10 mC Pyrrole Acetonitrile/LiClO4 | Edot-F6 100 mC Acetonitrile/LiClO4 | 150° | 0B |
| Steel | Plasma O2 | Decanoic acid | 10 mC Pyrrole Acetonitrile/LiClO4 | Edot-F6 100 mC Acetonitrile/LiClO4 | 154° | 0B |
| Steel | Plasma O2 | Undecylenic acid | 10 mC Pyrrole Acetonitrile/LiClO4 | Edot-F6 100 mC Acetonitrile/LiClO4 | 150° | 0B |
| Steel | Plasma O2 | Octadecyl phosphonic acid | 10 mC Pyrrole Acetonitrile/LiClO4 | Edot-F6 100 mC Acetonitrile/LiClO4 | 154° | 0B |
| Steel | | | 10 mC Pyrrole Water/H2SO4 | Edot-F6 100 mC Acetonitrile/LiClO4 | 150° | 0B |
| Steel | | | 10 mC Pyrrole Water/HFSO3 | Edot-F6 100 mC Acetonitrile/LiClO4 | 155° | 5B |
| Steel | | | 5 mC Pyrrole Water/oxalic acid | Edot-F4 10 mC Acetonitrile/LiClO4 | 160° | 5B |
| Steel | | Dopamine | | Edop-H8 200 mC Acetonitrile/Bu4NPF6 | 150° | 5B |
| Steel | | | 5 mC Pyrrole Water/paratoluene-sulfonic acid | Edot-F4 20 mC Acetonitrile/LiClO4 | 157° | 5B |
| Steel | Aqua regia | | 10 mC Pyrrole Acetonitrile/LiClO4 | Edot-F4 20 mC Acetonitrile/LiClO4 | 155° | 0B |
| Steel | | | Pyrrole/Aniline 7 mC water/Oxalic acid copolymer | Edot-F4 25 mC Acetonitrile/LiClO4 | 158° | 0B |

EXAMPLE 3: EXAMPLE OF PREPARATION OF SHORT-CHAIN FLUORINATED MONOMERS ACCORDING TO THE INVENTION AND STUDY OF ASSOCIATED PROPERTIES

For this example, in order to develop superoleophobic surfaces, EDOT-NH—$F_n$ monomers responding to the following general formula were synthesized and characterized:

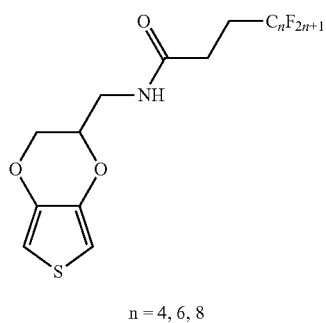

n = 4, 6, 8 a. Synthesis of the Compounds

The synthesis diagram of these compounds, in three steps, is presented below:

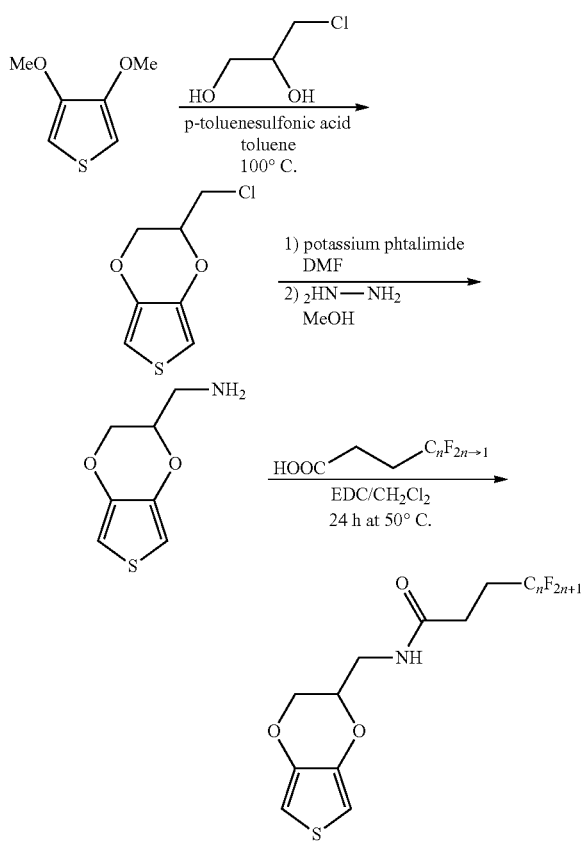

The first step of the synthesis is the transetherification of 3,4-dimethoxythiophene with 3-chloropropane-1,2-diol and enables 2-(chloromethyl)-2,3-dihydrothieno[3,4-b][1,4]dioxin to be obtained.

The second step is the substitution of the chloride group with a primary amine using the Gabriel reaction in the presence of potassium phthalamide.

2-(chloromethyl)-2,3-dihydrothieno[3,4-b][1,4]dioxin (0.3 g, 1.6 mmol) and potassium phthalamide (0.4 g, 2.2 mmol) are added to 5 mL of DMF. The mixture is heated at 100° C. for 24 hours.

Then, the solution is poured into 100 mL of water and the product is extracted with chloroform.

The organic layer is then washed with cold sodium hydroxide and water, then is dried on sodium sulfate $Na_2SO_4$.

The product obtained and the hydrazine hydrate (0.16 g, 3.2 mmol) are then added to 10 mL of methanol, the mixture is heated at 50° C. for 1 hour. 25 mL of water are added and the methanol is extracted under vacuum.

2 mL of concentrated HCl are then slowly added and the solution is heated at 60° C. for 1 hour.

After filtration, the filtrate is neutralized with 2N of sodium hydroxide. After evaporation of the solvent, the product is purified by column chromatography (silica gel, eluant: methanol/dichloromethane 1:4).

For these experiments, three fluorinated short chains, $C_4F_9$, $C_6F_{13}$ and $C_8F_{17}$, were introduced in order to demonstrate the possibility of producing superoleophobic surfaces with fluorinated short chains.

The following compounds were synthesized:
EDOT-NH2: (2,3-dihydrothieno[3,4-b][1,4]dioxin-2-yl)methanamine;
EDOT-NH-F8: N-((2,3-dihydrothieno[3,4-b][1,4]dioxin-2-yl)methyl)-4,4,5,5,6,6,7,7,8,8,9,9,10,10,11,11,11-heptadecafluoroundecanamide;
EDOT-NH-F6: N-((2,3-dihydrothieno[3,4-b][1,4]dioxin-2-yl)methyl)-4,4,5,5,6,6,7,7,8,8,9,9,9-tri-decafluorononanamide; and
EDOT-NH-F4: N-((2,3-dihydrothieno[3,4-b][1,4]dioxin-2-yl)methyl)-4,4,5,5,6,6,7,7,7-nonafluoro-heptanamide.

The applicant was able to demonstrate that fluorinated short-chain monomers may, under certain conditions, show liquid repellant properties superior to those of fluorinated long-chain compounds.

b. Surface Properties of the Compounds:

A deposition charge (Qs) of 100 mC/cm² was used for the deposit. The scanning electron microscope analyses of the polymer films showed that the length of the fluorinated chain had a major influence on the surface morphology. This is in particular shown in FIG. 10.

The increase in the length of the fluorinated chain induces a surface morphology change. A 3D assembly in the form of thin fibrils is observed for compounds C4F9 (FIG. 10*a-b*), while compounds C8F17 have a 3D assembly in the form of spheres (FIGS. 10*e-f*).

The surface wettability analyses were performed with four different liquid probes:
water ($\gamma L$=72.8 mN/m),
diidomethane ($\gamma L$=50.0 mN/m),
sunflower oil ($\gamma L$=31 mN/m),
hexadecane ($\gamma L$=27.6 mN/m).

The slip angles (α) and hysteresis (H) were determined using the tilted drop method with 6 μL of liquid drops. The slip angle corresponds to the minimal surface tilt for causing a water droplet to roll off.

The incoming and outgoing wetting angles, and consequently the hysteresis, were obtained just before the water drop rolls over the surface (the surface tilt causes a deformation of the drop).

At the time of deposition, superhydrophobic surfaces having self-cleaning properties were developed using three monomers ($\theta_{water}$=160.4°, $H_{water}$=1.3° and $\alpha_{water}$=1.2° for PEDOT-NH—$F_4$; $\theta_{water}$=160.5°, $H_{water}$=4.6° and $\alpha_{water}$=1.2° for PEDOT-NH—$F_6$; $\theta_{water}$=157.0°, $H_{water}$=8.0° and $\alpha_{water}$=1.4° for PEDOT-NH—$F_8$).

Surprisingly, when the surface tension of the liquid probe decreases (from water to hexadecane), a significant reduction in the liquid repellency was observed, with an increase in the length of the fluorinated chain.

The properties observed therefore contradict what is known for fluorinated polymers. In fact, contrary to what has been performed up to the present, for the first time, surfaces having excellent superoleophobic properties were successfully developed with extremely short fluorinated chains (F-butyl).

To fully understand the impact of each parameter on surface wettability, the influence of the surface morphology/roughness (physical part) and the intrinsic hydrophobicity of the polymers (chemical part) were separated.

To calculate these parameters, it is necessary to produce smooth surfaces of each polymer in order to measure their wettability. For this, "smooth" polymer surfaces could be obtained by reducing the deposition charge to around 0.5 mC/cm². The regularity of the surface was confirmed by optical profilometry.

Regardless of the liquid probe, a reduction in the hydro- and oleophobicity was observed with the length of the fluorinated chain.

The results of this work are presented in table 2 below.

TABLE 2

Water-repellent properties for "smooth" polymers; Qs = 0.5 mC/cm²

| | Static contact angles [deg] | | | |
|---|---|---|---|---|
| | Water | Diidomethane | Sunflower oil | Hexadecane |
| PEDOT-NH—$F_4$ | 93.3 | 62.6 | 51.9 | 43.4 |
| PEDOT-NH—$F_6$ | 102.5 | 68.3 | 60.3 | 49.1 |
| PEDOT-NH—$F_8$ | 113.7 | 79.7 | 65.7 | 54.0 |

To understand the importance of surface roughness on liquid repellency properties, depositions were performed by varying the deposition charge (Qs) from 0 to 400 mC/cm². FIGS. 11(a), 11(b) and 11(c) show the influence of Qs on the liquid repellency properties. As is illustrated in FIGS. 11(a), 11(b) and 11(c), the increase in the contact angle is not directly dependent on the deposition charge (Qs). The surface roughness, however, is dependent on the deposition charge (Qs).

The three polymers are intrinsically hydrophobic ($\theta_{water}$ "smooth" polymers>90°), which explains the ease of producing superhydrophobic surfaces from these monomers, as described by the theories of Wenzel and Cassie-Baxter.

To obtain superhydrophobic properties, deposition charges Qs of 25, 50 and 100 mC/cm² were necessary for obtaining the best water repellency properties with PEDOT-NH-F4, PEDOT-NH-F6 and PEDOT-NH-F8. Such deposition charges correspond to a surface roughness of around 0.10 μm, 0.15 μm and 2.2 μm, respectively. These analyses confirm the greatest capacity for producing superhydrophobic surfaces using EDOT-NH-F4 as a monomer.

Interestingly, it appears that the contact angle for diiodomethane for the three "smooth" polymers is largely under 90°, while structured polymers may push said liquid away with a contact angle greater than 140° C. This depends upon the deposition charge as shown in FIGS. 11(a) through (c) (for Qs≈50 mC/cm² with EDOT-NH-F4, 100 mC/cm² with EDOT-NH-F6 and 200 mC/cm² with EDOT-NH-F8).

Only the PEDOT-NH-F4 successfully repelled the sunflower oil with a maximum contact angle of 1500 when the Qs is 400 mC/cm², while the contact angle of the "smooth" PEDOT-NH-F4 is only 51.9°, as described in table 2 above.

For the two other polymers, the contact angle for sunflower oil with the structured polymers is less than 900 but greater than that of the corresponding "smooth" polymers, the values of which are presented in table 2 above.

With regard to hexadecane, only PEDOT-NH-F4 is capable of repelling said liquid. However, a strong dependence of the contact angle with the deposition charge Qs has been observed. In fact, due to the extremely low surface tension of the liquid probe, it is extremely sensitive to the roughness profile due to its high capacity for penetrating extremely small cavities. Atypically, a maximum contact angle of 132° was measured when Qs=100 mC/cm². For PEDOT-NH-F6 and PEDOT-NH-F8, the contact angle of the structured films is greater than that of the corresponding "smooth" polymers with a low Qs (low roughness), but becomes lower at a high Qs (high roughness).

The contact angle of the "smooth" polymers, the surface roughness and the surface tension of the liquid probe are important parameters, but are insufficient for predicting the possibility of producing superoleophobic surfaces.

The geometric parameters characterizing the surface morphology, such as the shape of the structures and their dimensions, are more important parameters than the liquid repellency power of the polymers.

In this example, it appears that the fibrils obtained with the $C_4F_9$ chains induce the formation of more re-entrant structures or having a negative geometry than the cauliflower structures obtained with C8F17 chains.

c. Physical and Chemical Parts of the Contact Angles:

The determination of the contact angles on "smooth" polymer surfaces made it possible to separate the percentage of the contribution of the surface physics (surface roughness/morphology) and the percentage of the contribution of the surface chemistry on the value of the contact angle.

The calculations were performed by taking into consideration the results obtained when Qs=100 mC/cm².

The results are presented in FIGS. 11(a) to (c).

The chemical contribution of the fluorinated polymers decreases with the γL of the liquid probe. It increases when the size of the fluorinated chain increases.

For the fluorinated polymers PEDOT-NH—$F_6$ and PEDOT-NH—$F_8$, it was observed that the physical contribution increases with the γL from water to diiodomethane, then decreases from diiodomethane to hexadecane. With hexadecane, the physical contribution represents around 10% of the contact angle for PEDOT-NH—$F_8$ and around 20% for PEDOT-NH—$F_6$.

For PEDOT-NH—$F_4$, the physical contribution increases with the γL from water to hexadecane. The physical contribution represents around 42% of the contact angle for water and 67% of the value of the contact angle for hexadecane.

If the physical contribution often represents less than 50% of the contact angles for the superhydrophobic surfaces, it should always be greater than 50% for the superoleophobic surfaces. In the present case, around ⅔ of the superoleophobic properties are due to the physical contribution, i.e. the surface roughness/morphology.

CONCLUSION

In this example, it has been demonstrated that it is possible to obtain surfaces that are superoleophobic with fluorinated short chains of the F-butyl type ($\theta_{sunflower\ oil}$=150.0° and $\theta_{hexadecane}$=132.1°).

This contradicts the current knowledge concerning fluorinated polymers and appears to be partially due to the presence of thin fibrils, as described above (cf. FIG. 10(a)).

In order to study the impact of the physical contribution (surface roughness/morphology) and the chemical contribution (intrinsic hydro/oleophobicity) on the contact angle, "smooth" polymer surfaces were produced and their properties were analyzed.

Such polymers are oleophilic (for F-butyl, $\theta_{sunflower\ oil}$=51.9° and $\theta_{hexadecane}$=43.4°). This means that it is the surface roughness and the morphology that are capable of modifying the properties of the surface by changing it from oleophilic to superoleophobic.

In this case, it also appears that the presence of amide connectors enables the mobility of the fluorinated chains to be reduced by increasing their crystallinity. This effect appears to be strongly amplified by the surface morphology and the roughness. Consequently, the amide connectors induce the formation of an additional energy barrier between the Cassie-Baxter state and the Wenzel state, which stabilizes the Cassie-Baxter state.

EXAMPLE 4: EXAMPLE OF SUPERHYDROPHOBIC SURFACES WITHOUT FLUORINE BASED ON 3,4-PROPYLENEDIOXYTHIOPHENE DERIVATIVES (PRODOT)

a. Synthesis of the Compounds:

The synthesis diagram of the ProDOT-H$_n$ compounds is presented below:

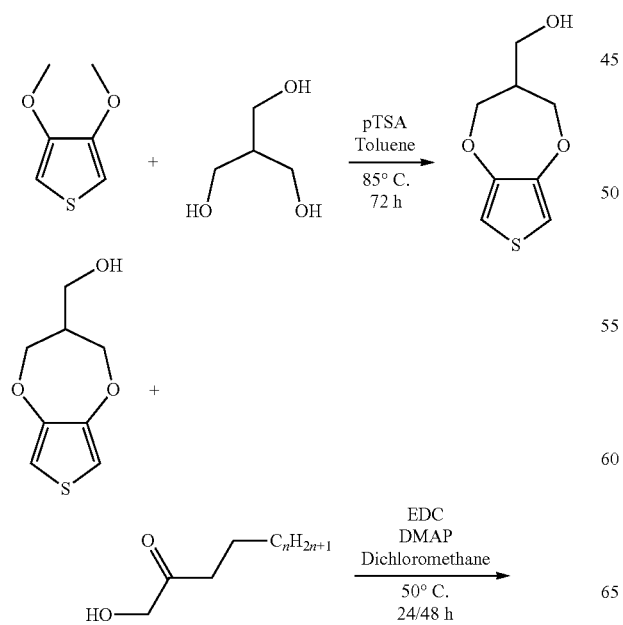

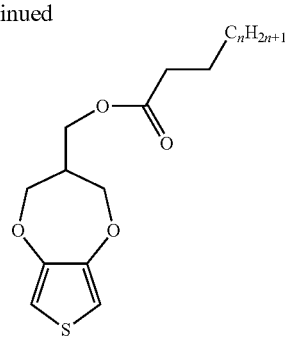

For the synthesis of the compounds, the ProDOT-OH ((3,4-dihydro-2H-thieno[3,4-b][1,4]dioxepin-3-yl)methanol hydroxylated precursor was obtained by transetherification of 3,4-dimethoxythiophene with 2-(hydroxymethyl)-propane-1,3-diol in toluene in the presence of a catalytic quantity of p-toluenesulfonic acid. Then, the original monomers (ProDOT-H$_n$ for which n=4, 6 and 8) were obtained by grafting of alkyl acids on ProDOT-OH by an esterification reaction in the presence of N-(3-dimethylamino-propyl)-N'-ethylcarbodiimide hydrochloride (EDC) and (dimethylamino) pyridine (DMAP) in dichloromethane.

The monomers are then purified by column chromatography (silica gel, eluant: dichloromethane/cyclohexane 9:1).

The general formula of the compounds obtained is as follows:

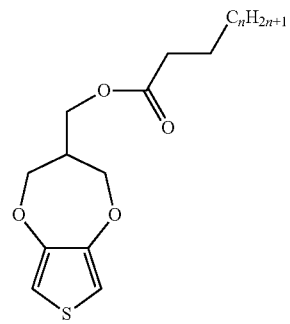

The compounds synthesized for this example are as follows:

ProDOT-H$_8$: (3,4-dihydro-2H-thieno[3,4-b][1,4]dioxepin-3-yl)methyl undecanoate;

ProDOT-H$_6$: (3,4-dihydro-2H-thieno[3,4-b][1,4]dioxepin-3-yl)methyl nonanoate; and ProDOT-H$_4$: (3,4-dihydro-2H-thieno[3,4-b][1,4]dioxepin-3-yl)methyl heptanoate.

The electropolymerization of the monomers was studied using two different solvents (acetonitrile and dichloromethane). All of the experiments were performed with 0.1 M of tetrabutylammonium hexafluorophosphate and 0.01 M of monomer in a three-electrode cell.

The working electrode is either a platinum disk enabling the electrochemical parameters of the monomers and polymers to be studied, or a gold plate enabling the properties of the electrolytic polymer films to be studied. The counter-electrode is a vitreous carbon rod and the reference electrode is a saturated calomel electrode.

First, the oxidation potential of the monomer was measured using a fast-scan cyclic voltammetry method (1 cycle of 0 to 2V at 0.1 Vs$^{-1}$). Then, to study the capacity of the films for polymerization, a slower cyclic voltammetry is performed: ten scans of −1V at a potential slightly lower than the oxidation potential of the monomer at 0.02 Vs$^{-1}$.

The same cyclic voltammetry experiment is also performed in a monomer-free solution, in order to verify the stability of the polymer.

To study the characteristics of the electrodeposited polymer surfaces, a gold plate of around 1 cm$^2$ replaces the platinum disk as the working electrode. The films are deposited using a chronoamperometry method with different deposition charges: 25, 50, 100, 200 and 300 mC/cm$^2$.

The surface wettability was determined by measuring the static contact angles (CA) on the water ($CA_{water}$; γL=72.8 mN/m).

The surface morphology was studied by scanning electron microscopy (SEM) and the roughness was evaluated by optical profilometry.

b. Electrochemistry:

The oxidation potentials of the different monomers, listed in table 3 below, are higher in dichloromethane than in acetonitrile. The capacity for electropolymerization is higher in acetonitrile than in dichloromethane.

TABLE 3

Oxidation potential of the monomers

| Polymer | $E^{CK}$ in acetonitrile [V vs. SCE] | $E^{CK}$ in dichloromethane [V vs. SCE] |
|---|---|---|
| ProDOT-H$_8$ | 1.56 | 1.91 |
| ProDOT-H$_6$ | 1.59 | 1.91 |
| ProDOT-H$_4$ | 1.58 | 1.91 |

The influence of the nature or the length of the hydrophobic substituents is negligible.

The polymer films were then electrodeposited by cyclic voltammetry (10 cycles) in order to study the growth and stability of the films.

FIG. 12 shows the cyclic voltammograms obtained for the polymers with oxidation and reduction peaks.

Each polymer is fully enlarged once in the acetonitrile and in the dichloromethane, constantly after each cycle.

In order to study their stability, the working electrode was placed in a monomer-free solution and ten cycles were performed in order to see whether there was any loss of a signal. The PProDOT-Hn are relatively stable in acetonitrile. However, they are less stable in dichloromethane because a fraction of polymer is detached after each cycle.

c. Surface Wetting Measurements

Different wetting measurements were performed for the polymers, in different solvents. The results of these tests are presented in table 4 below.

TABLE 4

Water repellency properties of the PProDOT polymers; Qs = 100 mC/cm2

| Polymer | Solvent | $CA_{water}/°$ | $H_{water}/°$ | $α_{water}/°$ |
|---|---|---|---|---|
| PProDOT-H$_8$ | Acetonitrile | 132.1 | — | |
| | Dichloromethane | 130.7 | — | |
| PProDOT-H$_6$ | Acetonitrile | 155.0 | Adhesion behavior | |
| | Dichloromethane | 129.3 | — | |
| PProDOT-H$_4$ | Acetonitrile | 117.4 | — | |
| | Dichloromethane | 118.6 | — | |

Table 4 above shows that the polymers PProDOT-H8 and PProDOT-H4 are hydrophobic, while the polymer PProDOT-H6 is superhydrophobic, with adhesion behavior. This means that a water drop remains attached to the surface, even if the surface is disturbed.

The electropolymerization solvent dichloromethane uniquely impacted the PProDOT-H$_6$ polymer, whereas, for the other PProDOT alkyl derivatives, no significant change in water contact angle is observed.

In other words, the electropolymerization in dichloromethane does not vary the wettability with water of the polymers PProDOT-H4 and PProDOT-H8, but has a significant impact on PProDOT-H6 (reduction by 25.7°).

d. Surface Morphology

To better understand the contact angle values, the surface morphology was studied by scanning electron microscopy (SEM).

FIG. 13 shows the SEM images of the PProDOT-Hn polymer surfaces.

The PProDOT-H6 polymer electrodeposited in acetonitrile is comprised of agglomerates or fibers on a layer of smaller nanofibers, the diameter of which is around 100 nm. The space between the aggregates appears to be the cause of the adhesion behavior of the PProDOT-H6 polymer surface.

From these images, it may be concluded that dichloromethane appears to influence the surface morphology of PProDOT hydrocarbon derivatives. These polymers produce more or less structured surfaces in the acetonitrile where, as in the dichloromethane, they are smooth with small holes that cover their entire surface, regardless of the length of the alkyl chain.

As is illustrated in FIGS. 14(a), (b) and (c), the diameter of the holes increases as when the hydrocarbon chain decreases. For PProDOT-H$_8$, the holes have a diameter of around 400 nm, for PProDOT-H$_6$, it is around 550 nm, and for PProDOT-H$_4$, the diameter is around 600 nm.

Consequently, if the effect of the solvent has already been identified as being a major factor in the electrodeposition of EDOT derivatives containing hydrocarbon chains (structured and smooth surfaces obtained in acetonitrile and dichloromethane, respectively), this example confirms that this is also the case for the experiments carried out.

In fact, it has been demonstrated that the solvent influences the solubility of the oligomers formed in the first instants. Under these electrochemical conditions, it has been demonstrated that the pore size is controlled by the length of the hydrocarbon chain grafted on the ProDOT polymerizable core.

The invention claimed is:

1. Multilayer superoleophobic and/or superhydrophobic material, including:
a first constituent that is a conductive substrate or a substrate previously rendered conductive, wherein (i) a surface of the first constituent is modified by a chemical and/or physical treatment, or (ii) the first constituent integrates a first adhesion-promoting conductive layer; and at least one other constituent that is a superoleophobic and/or superhydrophobic polymer or copolymer layer comprising one or more monomers based on an aromatic or heteroaromatic ring substituted by one or more fluorocarbon and/or hydrocarbon chains, wherein the different constituents of the material follow an increasing hydrophobicity gradient between a first layer deposited on a conductive substrate or a substrate previously rendered conductive and a last layer of the material.

2. Material according to claim 1, wherein the conductive substrate or a substrate previously rendered conductive is chosen from stainless or non-stainless steel, platinum, gold, silver, iron, indium and tin oxide ITO, titanium, vitreous carbon, silicon, aluminum, copper, zinc, nickel, brass and bronze.

3. Material according to claim 1, wherein the treatment is a chemical treatment performed by at least one of (i) polishing, (ii) sanding, (iii) brushing and (iv) a chemical attack with royal water *Aqua regia*.

4. Material according to claim 1, wherein the treatment is a physical treatment performed by oxygen plasma or argon plasma.

5. Material according to claim 1, wherein the adhesion-promoting conductive layer is deposited according to at least one technique selected from the group consisting of: self-assembled monolayer SAM, plasma, sol-gel, electrospinning, lithography, free radical polymerization, electrodeposition, layer-by-layer, dip-coating, and spin coating.

6. Material according to claim 5, wherein the at least one technique includes self-assembled monolayer SAM including undecylenic acid, undecanoic acid, decanoic acid, linoleic acid, octadecyl phosphonic acid, pyrrole undecanethiol, N-(3,4-dihydroxyphenethyl)thiophene-3-carboxamide, dopamine, taken alone or as a mixture.

7. Material according to claim 5, wherein the at least one technique includes electrodeposition with an electrodeposition layer comprised of one or more monomers based on an aromatic or heteroaromatic ring, optionally substituted.

8. Material according to claim 5, wherein the at least one technique includes electrodeposition with an electrodeposition layer comprised of one or more pyrrole or aniline monomers, taken alone or as a mixture.

9. Material according to claim 5, wherein the adhesion-promoting conductive layer has a thickness of 20 nm.

10. Material according to claim 9, wherein the adhesion-promoting conductive layer has a thickness of less than 100 nm.

11. Material according to claim 1, wherein the superoleophobic and/or superhydrophobic polymer or copolymer layer is comprised of one or a plurality of monomers having the following general formula (I):

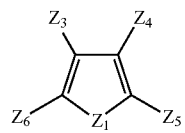

(I)

wherein:
$Z_1$ is chosen from the atoms and groups S, O, NH and N—W;
$Z_3$ is chosen from the atoms and groups H, $X_1$—W, $X_1$—$R_1$—$X_2$, $C(R_2)(R_3)$;
$Z_4$ is chosen from the groups W, $X_1$—W, $X_1$—$R_1$—$X_2$, $C(R_2)(R_3)$;
$Z_5$ and $Z_6$ represent an H atom or a hydrocarbon chain including 3 carbon atoms;
wherein:
W represents $(CF_2)_qF$, $B_1$—$(CY_2)_pY$, $Q_1$-$Z_2$ or $B_1$-$Q_1$-$Z_2$;
with $B_1$, $B_2$, $B_3$, identical or different, chosen from the groups: $C_1$-$C_{20}$ alkyls, $C_1$-$C_{20}$ alkenyls, $C_1$-$C_{20}$ alkynyls, $C_6$-$C_{18}$ aryls, $C_6$-$C_{18}$ heteroaryls;
with $Z_2$ corresponding to $A_1$, $CH(A_1)(A_2)$, $CH_2(A_1)$, $NH(A_1)$, $N(A_1)(A_2)$, $O(A_1)$ or $S(A_1)$;
for which $A_1$ and $A_2$, identical or different, represent:
—$B_2$—$(CY_2)_pY$,
—$B_3$-ph-$Q_2$-$B_2$—$(CY_2)_pY$; "ph" designating the functional phenyl group;
with q being between 1 and 20 and p between 0 and 20;
with Y corresponding to H or F, except when Y is an H atom, then p is equal to 0;
with $Q_1$ and $Q_2$, identical or different, which represent OC(O), C(O), SC(O), NHC(O);
$X_1$ and $X_2$; identical or different, are chosen from the atoms or groups O, S, NH;
$R_1$ is chosen from the groups —CH(W)—, —$(CH_2)_{n1}$—CH(W)—, —CH(W)—$(CH_2)_{n1}$, —$(CH_2)_{n2}$—CH(W)—$(CH_2)_{n3}$— and —$(CH_2)_{n1}$, when $Z_1$ equals N—W; W being as defined above and $n_1$, $n_2$, $n_3$, identical or different, are between 1 and 12, the sum of $n_2+n_3$ being less than or equal to 12;
$R_2$ is a hydrocarbon chain including 3 carbon atoms;
$R_3$ is chosen from the groups W, $X_1$—W or $X_1$—$R_1$—$X_2$;
and wherein:
when $Z_3$ and $Z_4$ correspond to $X_1$—$R_1$—$X_2$, they are linked to one another to form a ring;
when $Z_3$ and/or $Z_4$ correspond to $C(R_2)(R_3)$, they are linked to $Z_6$ and $Z_5$, ($Z_6$ and $Z_3$) and ($Z_5$ and $Z_4$), in order to form a 6-carbon aromatic ring, and when $R_3$ corresponds to $X_1$—$R_1$—$X_2$ then $Z_3$ and $Z_4$ are linked to one another and also form a ring;
taken together or as a mixture.

12. Material according to claim 11, wherein the superoleophobic and/or superhydrophobic polymer or copolymer layer is comprised of one or a plurality of monomers having the following general formula (I):
wherein:
$Z_1$ is chosen from the atoms and groups S, NH and N—W;
$Z_3$ is chosen from the atoms and groups H, $X_1$—W and $X_1$—$R_1$—$X_2$;
$Z_4$ is chosen from the groups W, $X_1$—W and $X_1$—$R_1$—$X_2$;
$Z_5$ and $Z_6$ represent an H atom;
wherein:
W represents $(CF_2)_qF$, $B_1$—$(CY_2)_pY$, $Q_1$-$Z_2$ or $B_1$-$Q_1$-$Z_2$;
with $B_1$, $B_2$, $B_3$, identical or different, chosen from the groups: $C_1$-$C_{16}$ alkyls, $C_1$-$C_{16}$ alkenyls, $C_1$-$C_{16}$ alkynyls, $C_6$-$C_{18}$ aryls, $C_6$-$C_{18}$ heteroaryls;
with $Z_2$ corresponding to $A_1$, $CH(A_1)(A_2)$, $CH_2(A_1)$, $NH(A_1)$, $N(A_1)(A_2)$, $O(A_1)$ or $S(A_1)$;
for which $A_1$ and $A_2$, identical or different, represent:
—$B_2$—$(CY_2)_pY$,
—$B_3$-ph-$Q_2$-$B_2$—$(CY_2)_pY$; "ph" designating the functional phenyl group;
with q being between 1 and 16 and p being between 0 and 16;
with Y corresponding to H or F, except when Y is an H atom, then p is equal to 0;
with $Q_1$ and $Q_2$, identical or different, which represent OC(O), C(O), SC(O), NHC(O);
$X_1$ and $X_2$, identical or different, are chosen from the atoms or groups O, S;
$R_1$ is chosen from the groups —CH(W)—, —$(CH_2)_{n1}$—CH(W)—, —CH(W)—$(CH_2)_{n1}$, —$(CH_2)_{n2}$—CH(W)—$(CH_2)_{n3}$— and —$(CH_2)_{n1}$— when $Z_1$ equals N—W; W being as defined above and $n_1$, $n_2$, $n_3$, identical or different, are between 1 and 4, the sum of $n_2+n_3$ being less than or equal to 4;

and wherein:
when $Z_3$ and $Z_4$ correspond to $X_1$—$R_1$—$X_2$, they are linked to one another to form a ring;

taken alone or as a mixture.

13. Material according to claim 12, wherein the superoleophobic and/or superhydrophobic polymer or copolymer layer is comprised of one or a plurality of monomers chosen from:

(i) the compounds of formula (I) wherein:
$Z_1$ is chosen from the atoms and groups S, NH and N—W;
$Z_3$ is chosen from the atoms and groups H, $X_1$—W, $X_1$—$R_1$—$X_2$;
$Z_4$ is chosen from the atoms and groups W, $X_1$—W, $X_1$—$R_1$—$X_2$;
$Z_5$ and $Z_6$ represent an H atom;
wherein:
W represents $(CF_2)_qF$, $B_1$—$(CF_2)_pF$, $Q_1$-$Z_2$ or $B_1$-$Q_1$-$Z_2$;
with $B_1$, $B_2$, $B_3$, identical or different, chosen from the groups: $C_1$-$C_{16}$ alkyls, $C_1$-$C_{16}$ alkenyls, $C_1$-$C_{16}$ alkynyls, $C_6$-$C_{18}$ aryls, $C_6$-$C_{18}$ heteroaryls;
with $Z_2$ corresponding to $A_1$, $CH(A_1)(A_2)$, $CH_2(A_1)$, $NH(A_1)$, $N(A_1)(A_2)$, $O(A_1)$ or $S(A_1)$;
for which $A_1$ and $A_2$, identical or different, represent:
—$B_2$—$(CF_2)_pF$,
—$B_3$-ph-$Q_2$-$B_2$—$(CF_2)_pF$; "ph" designating the functional phenyl group;
with q and p being between 7 and 16;
with $Q_1$ and $Q_2$, identical or different, which represent OC(O), C(O), SC(O), NHC(O);
$X_1$ and $X_2$, identical or different, are chosen from the atoms or groups O, S;
$R_1$ is chosen from the groups —CH(W)—, —$(CH_2)_{n1}$—CH(W)—, —CH(W)—$(CH_2)_{n1}$, —$(CH_2)_{n2}$—CH(W)—$(CH_2)_{n3}$— and —$(CH_2)_{n1}$— when $Z_1$ equals N—W; W being as defined above and $n_1$, $n_2$, $n_3$, identical or different, are between 1 and 4, the sum of $n_2+n_3$ being less than or equal to 4;
and wherein:
when $Z_3$ and $Z_4$ correspond to $X_1$—$R_1$—$X_2$, they are linked to one another to form a ring;

or from (ii) the following fluorine-free compounds, also responding to the general formula (I) wherein:
$Z_1$ is chosen from the atoms and groups S, O, NH and N—W;
$Z_3$ is chosen from the atoms and groups H, $X_1$—W, $X_1$—$R_1$—$X_2$, $C(R_2)(R_3)$;
$Z_4$ is chosen from the atoms and groups W, $X_1$—W, $X_1$—$R_1$—$X_2$, $C(R_2)(R_3)$;
$Z_5$ and $Z_6$ represent an H atom or a hydrocarbon chain including 3 carbon atoms;
wherein:
W represents $B_1$—H, $Q_1$-$Z_2$ or $B_1$-$Q_1$-$Z_2$;
with $B_1$, $B_2$, $B_3$, identical or different, chosen from the groups: $C_1$-$C_{20}$ alkyls, $C_1$-$C_{20}$ alkenyls, $C_1$-$C_{20}$ alkynyls, $C_6$-$C_{18}$ aryls, $C_6$-$C_{18}$ heteroaryls;
with $Z_2$ corresponding to $A_1$, $CH(A_1)(A_2)$, $CH_2(A_1)$, $NH(A_1)$, $N(A_1)(A_2)$, $O(A_1)$ or $S(A_1)$;
for which $A_1$ and $A_2$, identical or different, represent:
—$B_2$—H,
—$B_3$-ph-$Q_2$-$B_2$—H; "ph" designating the functional phenyl group;
with $Q_1$ and $Q_2$, identical or different, which represent OC(O), C(O), SC(O), NHC(O);
$X_1$ and $X_2$, identical or different, are chosen from the atoms or groups O, S, NH;
$R_1$ is chosen from the groups —CH(W)—, —CH(W)—$(CH_2)_{n1}$, —$(CH_2)_{n2}$—CH(W)—$(CH_2)_{n3}$—; and
—$(CH_2)_{n1}$— when $Z_1$ equals N—W; W being as defined above and $n_1$, $n_2$, $n_3$, identical or different, are between 1 and 12, the sum of $n_2+n_3$ being less than or equal to 12;
$R_2$ is a hydrocarbon chain including 3 carbon atoms;
$R_3$ is chosen from the groups W, $X_1$—W or $X_1$—$R_1$—$X_2$;
and wherein:
when $Z_3$ and $Z_4$ correspond to $X_1$—$R_1$—$X_2$, they are linked to one another to form a ring;
when $Z_3$ and/or $Z_4$ correspond to $C(R_2)(R_3)$, they are linked to $Z_6$ and $Z_5$, ($Z_6$ and $Z_3$) and ($Z_5$ and $Z_4$), to form a 6-carbon aromatic ring, and when $R_3$ corresponds to $X_1$—$R_1$—$X_2$, then $Z_3$ and $Z_4$ are linked to one another and also form a ring;

or from (iii) the following short-chain fluorinated compounds also responding to the general formula (I) wherein:
$Z_1$ is chosen from the atoms and groups S, O, NH and N—W;
$Z_3$ is chosen from the atoms and groups H, $X_1$—W, $X_1$—$R_1$—$X_2$, $C(R_2)(R_3)$;
$Z_4$ is chosen from the atoms and groups W, $X_1$—W, $X_1$—$R_1$—$X_2$, $C(R_2)(R_3)$;
$Z_5$ and $Z_6$ represent an H atom or a hydrocarbon chain including 3 carbon atoms;
wherein:
W represents $(CF_2)_qF$, $B_1$—$(CF_2)_pF$, $Q_1$-$Z_2$ or $B_1$-$Q_1$-$Z_2$;
with $B_1$, $B_2$, $B_3$, identical or different, chosen from the groups: $C_1$-$C_{20}$ alkyls, $C_1$-$C_{20}$ alkenyls, $C_1$-$C_{20}$ alkynyls, $C_6$-$C_{18}$ aryls, $C_6$-$C_{18}$ heteroaryls;
with $Z_2$ corresponding to $A_1$, $CH(A_1)(A_2)$, $CH_2(A_1)$, $NH(A_1)$, $N(A_1)(A_2)$, $O(A_1)$ or $S(A_1)$;
for which $A_1$ and $A_2$, identical or different, represent:
—$B_2$—$(CF_2)_pF$,
—$B_3$-ph-$Q_2$-$B_2$—$(CF_2)_pF$; "ph" designating the functional phenyl group;
with q and p being between 1 and 6;
with $Q_1$ and $Q_2$, identical or different, which represent OC(O), C(O), SC(O), NHC(O);
$X_1$ and $X_2$, identical or different, are chosen from the atoms or groups O, S, NH;
$R_1$ is chosen from the groups —CH(W)—, —$(CH_2)_{n1}$—CH(W)—, —CH(W)—$(CH_2)_{n1}$, —$(CH_2)_{n2}$—CH(W)—$(CH_2)_{n3}$—; and
—$(CH_2)_{n1}$— when $Z_1$ equals N—W; W being as defined above and $n_1$, $n_2$, $n_3$, identical or different, are between 1 and 12, the sum of $n_2+n_3$ being less than or equal to 12;
$R_2$ is a hydrocarbon chain including 3 carbon atoms;
$R_3$ is chosen from the groups W, $X_1$—W or $X_1$—$R_1$—$X_2$;
and wherein:
when $Z_3$ and $Z_4$ correspond to $X_1$—$R_1$—$X_2$, they are linked to one another to form a ring;
when $Z_3$ and/or $Z_4$ correspond to $C(R_2)(R_3)$, they are linked to $Z_6$ and $Z_5$, ($Z_6$ and $Z_3$) and ($Z_5$ and $Z_4$), to form a 6-carbon aromatic ring, and when $R_3$ corresponds to $X_1$—$R_1$—$X_2$, then $Z_3$ and $Z_4$ are linked to one another and also form a ring;
taken alone or as a mixture.

14. Material according to claim 13, wherein the superoleophobic and/or superhydrophobic polymer or copolymer layer is comprised of one or a plurality of monomers chosen from the following fluorine-free compounds, having the general formula (I) wherein:
$Z_1$ is chosen from the atoms and groups S, NH and N—W;
$Z_3$ is chosen from the atoms and groups H, $X_1$—W, $X_1$—$R_1$—$X_2$;
$Z_4$ is chosen from the atoms and groups W, $X_1$—W, $X_1$—$R_1$—$X_2$;
$Z_5$ and $Z_6$ represent an H atom;
wherein:
W represents $B_1$—H, $Q_1$-$Z_2$ or $B_1$-$Q_1$-$Z_2$;
with $B_1$, $B_2$, $B_3$, identical or different, chosen from the groups: $C_1$-$C_{16}$ alkyls, $C_1$-$C_{16}$ alkenyls, $C_1$-$C_{16}$ alkynyls, $C_6$-$C_{18}$ aryls, $C_6$-$C_{18}$ heteroaryls;
with $Z_2$ corresponding to $A_1$, $CH(A_1)(A_2)$, $CH_2(A_1)$, $NH(A_1)$, $N(A_1)(A_2)$, $O(A_1)$ or $S(A_1)$;
for which $A_1$ and $A_2$, identical or different, represent:
—$B_2$—H,
—$B_3$-ph-$Q_2$-$B_2$—H; "ph" designating the functional phenyl group;
with $Q_1$ and $Q_2$, identical or different, which represent OC(O), C(O), SC(O), NHC(O);
$X_1$ and $X_2$, identical or different, are chosen from the atoms or groups O, S;
$R_1$ is chosen from the groups —CH(W)—, —$(CH_2)_{n1}$—CH(W)—, —CH(W)—$(CH_2)_{n1}$, —$(CH_2)_{n2}$—CH(W)—$(CH_2)_{n3}$— and —$(CH_2)_{n1}$— when $Z_1$ equals N—W; W being as defined above and $n_1$, $n_2$, $n_3$, identical or different, are between 1 and 4, the sum of $n_2$+$n_3$ being less than or equal to 4;
and wherein:
when $Z_3$ and $Z_4$ correspond to $X_1$—$R_1$—$X_2$, they are linked to one another to form a ring;
or from the following short-chain fluorinated compounds also responding to the general formula (I), wherein:
$Z_1$ is chosen from the atoms and groups S, NH and N—W;
$Z_3$ is chosen from the atoms and groups H, $X_1$—W, $X_1$—$R_1$—$X_2$;
$Z_4$ is chosen from the atoms and groups W, $X_1$—W, $X_1$—$R_1$—$X_2$;
$Z_5$ and $Z_6$ represent an H atom;
wherein:
W represents $(CF_2)_4F$, $B_1$—$(CF_2)_4F$, $Q_1$-$Z_2$ or $B_1$-$Q_1$-$Z_2$;
with $B_1$, $B_2$, $B_3$, identical or different, chosen from the groups: $C_1$-$C_{14}$ alkyls;
with $Z_2$ corresponding to $A_1$, $CH(A_1)(A_2)$, $CH_2(A_1)$, $NH(A_1)$, $N(A_1)(A_2)$, $O(A_1)$ or $S(A_1)$;
for which $A_1$ and $A_2$, identical or different, represent:
—$B_2$—$(CF_2)_4F$,
—$B_3$-ph-$Q_2$-$B_2$—$(CF_2)_4F$; "ph" designating the functional phenyl group;
with $Q_1$ and $Q_2$, identical or different, which represent OC(O), C(O), SC(O), NHC(O);
$X_1$ and $X_2$, identical or different, are chosen from the atoms or groups O, S;
$R_1$ is chosen from the groups —CH(W)—, —$(CH_2)_{n1}$—CH(W)—, —CH(W)—$(CH_2)_{n1}$, —$(CH_2)_{n2}$—CH(W)—$(CH_2)_{n3}$— and —$(CH_2)_{n1}$— when $Z_1$ equals N—W; W being as defined above and $n_1$, $n_2$, $n_3$, identical or different, are between 1 and 4, the sum of $n_2$+$n_3$ being less than or equal to 4;
and wherein:
when $Z_3$ and $Z_4$ correspond to $X_1$—$R_1$—$X_2$, they are linked to one another to form a ring;
taken alone or as a mixture.

15. Process for producing a superoleophobic and/or superhydrophobic material including:
performing at least one of (i) a physical and/or chemical treatment of a conductive substrate or a substrate previously rendered conductive and (ii) deposition of an adhesion-promoting conductive layer on the substrate;
depositing, on the adhesion-promoting conductive layer, at least one superoleophobic and/or superhydrophobic polymer or copolymer layer comprised of one or more monomers based on an aromatic or heteroaromatic ring substituted by one or more fluorocarbon and/or hydrocarbon chains; and
recovering the superoleophobic and/or superhydrophobic material,
wherein the superoleophobic and/or superhydrophobic material is a material according to claim 1.

16. The material according to claim 1, which is in the form of an anti-adhesion material.

17. The material according to claim 1, which is in the form of an anti-friction material.

18. The material according to claim 1, which is in the form of an anti-corrosion material.

19. Material according to claim 2, wherein the adhesion-promoting conductive layer is deposited according to at least one technique selected from the group consisting of: self-assembled monolayer SAM, plasma, sol-gel, electrospinning, lithography, free radical polymerization, electrodeposition, layer-by-layer, dip-coating, and spin coating.

20. Material according to claim 19, wherein the at least one technique includes self-assembled monolayer SAM including undecylenic acid, undecanoic acid, decanoic acid, linoleic acid, octadecyl phosphonic acid, pyrrole undecanethiol, N-(3,4-dihydroxyphenethyl)thiophene-3-carboxamide, dopamine, taken alone or as a mixture.

\* \* \* \* \*